(12) United States Patent
Thompson et al.

(10) Patent No.: US 7,034,013 B2
(45) Date of Patent: Apr. 25, 2006

(54) FORMULATIONS CONTAINING PROPOFOL AND A SULFOALKYL ETHER CYCLODEXTRIN

(75) Inventors: Diane O. Thompson, Overland Park, KS (US); Gerold L. Mosher, Kansas City, MO (US)

(73) Assignee: Cydex, Inc., Lenexa, KS (US)

( * ) Notice: Subject to any disclaimer, the term of this patent is extended or adjusted under 35 U.S.C. 154(b) by 0 days.

(21) Appl. No.: 10/102,066

(22) Filed: Mar. 19, 2002

(65) Prior Publication Data

US 2003/0073665 A1    Apr. 17, 2003

Related U.S. Application Data

(60) Provisional application No. 60/277,305, filed on Mar. 20, 2001.

(51) Int. Cl.
*A61K 31/724* (2006.01)
*A61K 31/04* (2006.01)

(52) U.S. Cl. .......................... 514/58; 514/734
(58) Field of Classification Search .............. 514/58, 514/734
See application file for complete search history.

(56) References Cited

U.S. PATENT DOCUMENTS 5,134,127 A * 7/1992 Stella et al. ................. 514/58
5,962,536 A * 10/1999 Komer ........................ 514/731

FOREIGN PATENT DOCUMENTS

WO    PCT/GB96/00737    10/1996
WO    01/97796 A1    12/2001

OTHER PUBLICATIONS

MacKenzie, C.R. et al., Formulation and Evaluation of a propanidid hydroxypropyl- B-cyclodextrin solution for intravenous anaesthesia, International Journal of Pharmaceutics, 1997, vol. 159, 191-196.

Miyoshi, M. et al. , Alkalinizing Water-Soluble Local Anesthetic Solutions by Addition of Cyclodextrin, Regional Anesthesia and Pain Medicine, 1998, 23 (2): 176-181.

Picard, Pascale et al., Prevention of Pain on Injection with Propofol: A Quantitative Systematic Review, Anesth Analg, 2000, 90:963-969.

Doenicke, A. et al., A Comparison of Two Formulations for Etomidate . . . , Anesth Analg, 1994, 79:933-939.

James, M.F.M. et al., Heart Block Following Propofol: A Case Report, Br j Anaesth, 1989, 62:213-215.

Talmage, D.E. et al., Asysytole After Anesthesia Induction with a Fentanyl, Propofol, and Succinylcholine Sequence, Anesth Analg, 1991, 73: 818-820.

Trapani, G. et al. Inclusion Complexation of Propofol with 2-Hydroxypropyl . . . , Journal of Pharmaceutical Sciences, Apr. 1998, vol. 87, No. 4: 514-518.

Bielen, S.J. et al., The Effect of a Cyclodextrin Vehicle . . . , Anesth Analg 1996, 82: 920-924.

Viernstein, H. et al., Preparation and Central Action of Propofol . . . , Arzneim-Forsch/Drug Res. 1993, 43, (11) Nr.S., 818-821.

Okimoto, K.; Rajewski, R. A.; Jona, J. A.; Stella, V. J. The interaction of charged and uncharged drugs with a neutral (HP-b-CD) and anionically charged (SBE7-b-CD) b-cyclodextrin. Pharmaceutical Research 1996, 13, (2), 256-264.

Loftsson, T.; Peterson, D. S. Cyclodextrin Solubilization of Eth-615, a Zwitterionic Drug. Drug Development and Industrial Pharmacy 1998, 24, (4), 365-370.

Loftsson, T.; Petersen, D. S. Cyclodextrin solubilization of water-insoluble drugs. Calcipotriol and EB-1089. Pharmazie 1997, 52, (10), 783-785.

(Continued)

*Primary Examiner*—Leigh C. Maier
(74) *Attorney, Agent, or Firm*—Rick Matos; Innovar, L.L.C.

(57) ABSTRACT

An injectable formulation of a sedative hypnotic drug, such as the anesthetic drug propofol, that is pharmaceutically stable and demonstrates a reduced incidence of pain upon injection. The formulation of the present invention employs a sulfoalkyl ether cyclodextrin solubilizing and complexing excipient, such as CAPTISOL® cyclodextrin (sulfobutyl ether β-cyclodextrin) to form a true aqueous solution and not a suspension. This formulation minimizes the allergic response and microbial contamination issues typically associated with propofol parenteral formulations. The present formulation may also reduce pain on injection as compared to the known emulsion type propofol formulations. The liquid formulation can be sterile filtered unlike emulsion-type formulations of sedative hypnotics. The liquid formulation can be lyophilized or otherwise dried to yield a solid formulation.

61 Claims, 3 Drawing Sheets

OTHER PUBLICATIONS

Savolainen, J.; Jarvinen, K.; Matilainen, L.; Jarvinen, T. Improved Dissolution and Bioavailability of Phenytoin by Sulfobutylether-Beta-Cyclodextrin ((Sbe)(7m)-Beta-Cd) and Hydroxypropyl-Beta-Cyclodextrin (Hp-Beta-Cd) Complexation. International Journal of Pharmaceutics 1998, 165, (1), 69-78.

Arima, H.; Yunomae, K.; Miyake, K.; Irie, T.; Hirayama, F.; Uekama, K. Comparative Studies of the Enhancing Effects of Cyclodextrins on the Solubility and Oral Bioavailability of Tacrolimus in Rats. Journal of Pharmaceutical Sciences 2001, 90, (6), 690-701.

Lyons, R.; Trogden, J.; Duggirala, M.; Welty, D.; Chang, J.; Olejnik, O. Development of a Cyclodextrin-Based Prednisolone Acetate Solution for Ocular Administration. Presented at the *AAPS Annual Meeting and Exposition*, Oct. 21-25, 2001, Denver CO.

Zhao, L. W.; Li, P.; Yalkowsky, S. H. Solubilization of Fluasterone. Journal of Pharmaceutical Sciences 1999, 88, (10), 967-969.

Chan, L. W.; Kurup, T. R. R.; Muthaiah, A.; Thenmozhiyal, J. C. Interaction of P-Hydroxybenzoic Esters With Beta-Cyclodextrin. International Journal of Pharmaceutics 2000, 195, (1-2), 71-79.

Loftsson, T.; Stefansdottir, O.; Frioriksdottir, H.; Guomundsson, O. Interactions between preservatives and 2-hydroxypropyl beta-cyclodextrin . Drug Development and Industrial Pharmacy 1992, 18, (13), 1477-1484.

Dollo, G.; Le Corre, P.; Chevanne, F.; Le Verge, R. Complexation Between Local Anaesthetics and Beta-Cyclodextrin Derivatives—Relationship Between Stability Constants and in Vitro Membrane Permeability of Bupivacaine and Lidocaine From Their Complexes. Stp Pharma Sciences 1998, 8, (3), 189-195.

Dollo, et al., "Inclusion complexation of amide-type local anesthetics with beta-cyclodextrin and its derivatives. II. Evaluation of affinity constants and in vitro transfer rate constants", (*International Journal of Pharmaceutics*, 136 (1996) 165-174).

Li, et al., "Determination of the binding constant for the inclusion complex between procaine hydrochloride and beta-cyclodextrin by capillary electrophoresis", (*Talanta*, 59 (2003) 493-499).

* cited by examiner

FORMULATIONS CONTAINING PROPOFOL AND A SULFOALKYL ETHER CYCLODEXTRIN

Applications hereby claim the PROIORITY of Provisional Application for patent Ser. No. 60/277,305 filed Mar. 20, 2001 in the name of the above-identified inventors.

FIELD OF THE INVENTION

The present invention relates to anesthetic liquid formulations and in particular to a parenteral formulation containing a sedative hypnotic agent, such as propofol, and a sulfoalkyl ether cyclodextrin and to the use of this formulation.

BACKGROUND OF THE INVENTION

Propofol (2,6-diisopropylphenol or 2,6-bis(1-methylethyl)-phenol)) is an injectable potent, short-acting, non-barbiturate sedative-hypnotic agent for use in the induction and maintenance of anesthesia or sedation. Intravenous injection of a therapeutic dose of propofol rapidly induces anesthesia usually within 40 seconds from the start of injection. As with other rapidly acting intravenous anesthetic agents, the half-time of the blood-brain equilibrium is approximately 1 to 3 minutes and this accounts for the rapid induction of anesthesia.

Propofol can undergo an oxidative process to produce the dimer, 4,4'-dihydroxy-3,3',5,5'-tetraisopropyl-biphenyl. This dimer is visually detected at low concentrations by the appearance of a yellow color in a solution containing propofol. The degradation of propofol is thought to occur through a free radical reaction that may be catalyzed by light, oxidation or the presence of divalent or trivalent cations.

The currently marketed DIPRIVAN® formulation of propofol is an opaque oil-in-water emulsion containing lipids and egg lecithin as an emulsifying agent. The DIPRIVAN® emulsion-type formulation contains 10 mg/mL propofol, 100 mg/mL soybean oil, 22.5 mg/mL glycerol, 12 mg/mL egg lecithin and 0.005% w/v disodium edetate (EDTA) at a pH of 7.0 to 8.5. It is packaged under nitrogen headspace in single use containers. Even though it is a sterile product, the DIPRIVAN® formulation can support microbial growth as it is not an antimicrobially preserved product under USP standards. The formulation also has problems concerning allergic response to the egg components, and the moderate to high incidence of pain on injection.

Emulsion formulations are typically problematic with regard to microbial growth, not only because the lipid components can readily support the growth, but because 0.22 micron or smaller "sterilizing" filters cannot be used. A filter pore size of $\geq 5$ µm is recommended for the marketed formulation "unless it has been demonstrated that the filter does not restrict the flow . . . and/or cause the breakdown of the emulsion" (DIPRIVAN® Injectable Emulsion Propofol, Professional Information Brochure, Zeneca Pharmaceuticals, April 2001). Propofol was originally marketed as the emulsion with no preservative. However, concerns over potential contamination problems observed after approval of the NDA led the manufacturer to withdraw the formulation and replace it with one containing the preservative EDTA.

A generic formulation has recently been approved and marketed, in which the pH is lowered to the range of 4.5 to 6.4, and the preservative EDTA has been replaced with sodium metabisulfite at 0.25 mg/mL. In the absence of a solubilizing agent, the water solubility of propofol is approximately 0.154 mg/mL. Thus these two formulations are both prepared as oil in water emulsions, with most of the propofol being solubilized by the lipid phase. The preservatives have been added to inhibit microbial growth. The EDTA formulations are disclosed in U.S. Pat. No. 5,714,520, No. 5,731,355, No. 5,731,356 and No. 5,908,869 to Jones et al.

A number of other patents disclose different propofol formulations reportedly having improved stability as compared to conventional emulsion-type formulations. U.S. Pat. No. 6,028,108 to George discloses an oil-in-water emulsion formulation containing propofol and pentetate. U.S. Pat. No. 6,100,302 to Pejaver et al. discloses an oil-in-water formulation containing propofol and soybean oil. U.S. Pat. Nos. 6,140,373 and 6,140,374 to May et al. discloses an oil-in-water formulation containing propofol and an antimicrobial agent. U.S. Pat. No. 6,147,122 to Mirejovsky et al. discloses an oil-in-water emulsion containing propofol and sodium bisulfite, potassium metabisulfite, potassium sulfite, or sodium sulfite as antioxidant or antimicrobial preservative. U.S. Pat. No. 5,637,625 to Haynes discloses a microdroplet formulation containing propofol. None of these references suggests or discloses the non-emulsion formulation of the present invention.

Concerns also exist regarding the potential for allergies to the egg components of the emulsion and to the bisulfite used as a preservative in the generic formulation, as well as the potential for hyperlipidemia such as the propofol infusion syndrome reported in children (Bray, R. J., "Propofol infusion syndrome in children" Paediatr. Anaesth. (1998); 8;491–499). Elimination of the lipids and the emulsion formulation would lead to a superior and potentially safer product.

The marketed formulation of propofol is associated with significant incidence of pain on injection (P. Picard et al. in Anesth. Analg. (2000), vol. 90, pp. 963–969). The incidence of painful reactions after injection of propofol into the small dorsal veins of the hand is 30%–70% (R. A. Johnson et al. in Anaesth. (1990), 45:439–442; P. Barker et al. in Anaesth. (1991) 46:1069–1070; S. Y. King et al. in Anesth. Analg. (1992) 74:246–249). With injection into larger proximal veins, the probability of a painful reaction is 0%–30% (M. J. McCullought et al. in Anaesthesia (1985) 40:1117–1120; R. P. Scott et al. in Anaesthesia (1988) 43:92–94; C. H. McLeskey et al. in Anesth. Analg. (1993) 77(Suppl):S3–9).

Numerous approaches have been tested in an attempt to reduce the incidence of side effects associated with administration of propofol by injection. Some of these methods include: 1) dilution of the propofol formulation with 5% glucose and slow administration of the resulting mixture (D. N. Stokes et al., "Effect of diluting propofol on the incidence of pain on injection", Anaesth. (1989) 62:202–203); 2) use of cold isotonic saline (P. Barker et al., "Effect of prior administration of cold saline on pain during propofol injection: A comparison with cold propofol and propofol with lignocaine", *Anaesth.* (1991) 46:1069–1070); 3) pretreatment of the injection site with another agent (S. Y. King et al., "Lidocaine for the Prevention of Pain Due to Injection of Propofol", *Anesth. Analg.* (1992) 74:246–249; M. E. Nicol et al., "Modification of Pain on Injection of Propofol—A Comparison between Lignocaine and Procaine", *Anaesthesia* (1991) 46:67–69; W. A. Alyafi et al., "Reduction of Propofol Pain—Fentanyl vs Lidocaine", *Middle East J. Anesthesiol.* (1996) 13:613–619; N. M. Gajraj et al., "Preventing Pain During Injection of Propofol: The Optimal dose of Lidocaine", *J. Clin. Anesth.* (1996) 8:575–577; D. S. McDonald et al., "Injection Pain with Propofol. Reduction with Aspiration of Blood", *Anaesthesia* (1996) 51:878–880; M. H. Nathanson et al., "Prevention of Pain on Injection of Propofol: A Comparison of Lidocaine with Alfentanil", *Anesth. Analg.* (1996) 82:469–471; R. D. Haugen et al., "Thiopentone Pretreatment for Propofol Injection Pain in Ambulatory Patients", *Can. J. Anaesth.* (1995) 42:1108–1112, 1995; M. Dru et al., "The Effect of Alfentanil on Pain Caused by the Injection of Propofol During Anesthesia Induction in Children", *Can. Anesthesiol.* (1991) 39:383–386; R. P. Scott et al., "Propofol: Clinical Strategies of Preventing the Pain on Injection", *Anaesthesia* (1988) 43:92–94; D. Wilkinson et al., "Pain on Injection of Propofol: Modification by Nitroglycerin", *Anesth. Analg.* (1993) 77:1139–1142); 4) cooling of the propofol containing solution to 4° C. prior to injection (A McCrirrick et al., "Pain on Injection of Propofol: The Effect of Injectate Temperature", *Anaesthesia* (1990) 45:443–444); 5) warming of the propofol containing solution to 37° C. prior to injection (G. C. Fletcher et al., "The Effect of Temperature Upon Pain During Injection of Propofol", *Anaesthesia* (1996) 51:498–499); 6) mixing of the propofol containing solution with another active agent (G. Gehan et al., "Optimal Dose of Lignocaine for Preventing Pain on Injection of Propofol", *Br. J. Anaesthes.* (1991) 66:324–326; G. Zaouk et al., "Alizaprode Does Reduce Pain on Injection of Propofol—Comparison with Lidocaine", *Br. J. Anaesth.* (1993) 70:P6; B. Lyons et al., "Modification of Pain on Injection of Propofol. A Comparison of Pethidine and Lignocaine", *Anaesthesia* (1996) 51:394–395); and 7) adjustment of the pH of the propofol containing solution prior to injection (M. Eriksson et al., "Effect of lignocaine and pH on propofol-induced pain", *Br. J. Anaesth.* (1997) 78:502–506).

A number of researchers have investigated the hypothesis that the pain is associated with the concentration of free (not located in the lipid phase) propofol in the formulation. Doenicke, et. al. (Reducing Pain During Propofol Injection; The Role of the Solvent *Anesth. Analg.* (1996) 82:472–474) added saline or increasing amounts of long chain triglyceride emulsion to the marketed formulation in an attempt to shift the free propofol into the added lipid. The formulations were administered into a dorsal vein of the hand and the patients reported their pain during injection as none, mild, moderate or severe. The results indicate that pain was decreased as the lipid content in the formulation increased (and the concentration of propofol in the aqueous phase decreased).

Although several of these approaches have shown the ability to reduce the pain on injection observed with propofol, all have the disadvantage of requiring additional manipulation, which may or may not alter the pharmacokinetics and pharmacodynamics and makes delivery of anesthetics less efficient. Furthermore, the use of additional excipients may cause other side effects, such as hyperlipidemia. From a pharmacoeconomic viewpoint, additional manipulation and/or use of added components only increases the cost of treatment. Clearly a single, simple formulation demonstrating reduced pain on injection would be preferred.

Any reformulation of a drug has the ability to alter the drug's pharmacokinetics and pharmacodynamics. The potential for this is an obvious concern when one replaces an emulsion formulation with a true solution formulation. Several investigators have evaluated the effects of different emulsion or Cremophor® formulations on the pharmacokinetics (PK) and pharmacodynamics (PD) of propofol in rats (S. Dutta et al. in *J. Pharm. Sci.* (1997) 86(8):967–968; E. H. Cox et al. in *Pharm. Res.* (1998) 15(3):442–448). In a recent study (T. W. Schnider et al. in *Anesth.* (1998) 88:1170–1182), the effects of the additive EDTA, age, and method of administration on PK/PD were also examined in humans. The conclusion reached in each of these studies was that there were no changes in the PK/PD between the different formulations. There were, however, changes as a result of the method of administration (bolus vs. infusion).

U.S. Pat. No. 4,452,817 to Glen et al. discloses parenteral formulations containing propofol and solid diluent, a sterile water miscible solvent, an aqueous solution and/or a surfactant.

When the comparison was made between the marketed formulation and an in-situ prepared "lipid-free" formulation, there was a tendency for the lipid free formulation to demonstrate delayed onset of action and recovery in rats (S. Dutta et al. in *Anesth.* (1997) 87(6):1394–1405). This was confirmed in additional studies where an increase in volume of distribution and reduced potency was also seen with the lipid free formulation (S. Dutta et al. in *J. Pharm. Pharmacol.* (1998) 50:37–42). In each of these last two studies, the lipid free formulation was formed at the point of entry into the body. The propofol was diluted in ethanol and pumped into a mixing tee tube. A carrier solvent of water, glycerol and dextrose was pumped into the tee from another pump. The mixture passed from the tee directly to the rat. There was no confirmation that a true solution existed. It is very possible that propofol did not remain in solution, and that fact alone could explain the observed changes in PK/PD.

Numerous studies have reported on the success of formulations containing cyclodextrins and cyclodextrin derivatives to reduce tissue damage and pain following intramuscular injection (T. Irie et al. *J. Pharmacobio-Dyn.* (1983) 6(10):790–2; K. Masuda et al. in *Yakugaku Zasshi* (1984) 104(10):1075–82; A. Yoshida et al. in *Chem. Pharm. Bull.* (1990) 38(l):176–9) and intradermal injection (U.S. Pat. No. 5,602,112 to J. Rubinfeld). The intramuscular studies evaluated the tissue irritation after drugs were administered as suspensions in saline, or solubilized as complexes with β-cyclodextrin or 2-hydroxypropyl-β-cyclodextrin in water. The formulations containing the drugs complexed with the cyclodextrins showed reduced visual signs of irritation and tissue damage as compared to the formulations in saline. No assessment was made of pain. These studies show reduced tissue damage from cyclodextrin complexation, but only after 2 days of localized contact. The intradermal studies evaluated the ulcerative effects of several cytotoxic compounds, formulated with or without cyclodextrins, after administration into the skin of rats. Again, no measurement of pain was taken and the irritation evaluation was conducted only after contact times of 1 to 20 days. None of these studies evaluated the effects of cyclodextrin complexation on the pain associated with injection, especially after rapid intravenous administration or a continuous intravenous infusion.

Cyclodextrins are cyclic carbohydrates derived from starch. The unmodified cyclodextrins differ by the number of glucopyranose units joined together in the cylindrical structure. The parent cyclodextrins contain 6, 7, or 8 glucopyranose units and are referred to as α-, β-, and γ-cyclodextrin respectively. Each cyclodextrin subunit has secondary hydroxyl groups at the 2 and 3 positions and a primary hydroxyl group at the 6 position. The cyclodextrins may be pictured as hollow truncated cones with hydrophilic exterior surfaces and hydrophobic interior cavities. In aqueous solutions, these hydrophobic cavities provide a haven for hydrophobic organic compounds that can fit all or part of their structure into these cavities. This process, known as inclusion complexation, may result in increased apparent aqueous solubility and stability for the complexed drug. The complex is stabilized by hydrophobic interactions and does not involve the formation of any covalent bonds.

This dynamic and reversible equilibrium process can be described by Equations 1 and 2, where the amount in the complexed form is a function of the concentrations of the drug and cyclodextrin, and the equilibrium or binding constant, $K_b$. When cyclodextrin formulations are administered by injection into the blood stream, the complex rapidly dissociates due to the effects of dilution and non-specific binding of the drug to blood and tissue components.

$$\text{Drug} + \text{Cyclodextrin} \xrightleftharpoons{K_b} \text{Complex} \quad \text{Equation 1}$$

$$K_b = \frac{[\text{Complex}]}{[\text{Drug}][\text{Cyclodextrin}]} \quad \text{Equation 2}$$

The underivatized parent cyclodextrins are known to interact with and extract cholesterol and other membrane components, particularly upon accumulation in the kidney tubule cells, leading to toxic and sometimes fatal renal effects. Chemical modification of the parent cyclodextrins (usually at the hydroxyls) has resulted in derivatives with improved safety while retaining or improving the complexation ability. Of the numerous derivatized cyclodextrins prepared to date, only two appear to be commercially viable: the 2-hydroxypropyl derivatives (HP-β-CD; neutral cyclodextrins being commercially developed by Janssen and others), and the sulfoalkyl ether derivatives, such as sulfobutyl ether, (SBE-CD; anionic cyclodextrins being developed by CyDex, Inc.) However, the HP-β-CD still possesses toxicity that the SBE-CD does not.

The PK/PD of cyclodextrin containing propofol formulations has been evaluated. In a comparison study of the marketed formulation with one containing HP-β-CD, the effects of the formulation on cardiac changes in the rat were monitored. A substantial bradycardia of short (1–6 seconds) duration was observed following administration of the HP-β-CD formulation (S. J. Bielen et al. in *Anesth. Analg.* (Baltimore) (1996) 82(5):920–924). Bradycardia was not observed with the marketed formulation. A comparable study in rabbits showed no changes in PK or PD for the HP-β-CD containing formulation (H. Viernstein et al. in *Arzneim.-Forsch.* (1993) 43(8):818–21). However, there have been many reports of sudden bradycardia and asystole in patients under propofol anesthesia using the marketed formulation (T. D. Egan et al. in *Anesth. Analg.* (1991) 73:818–820; M. F. M. James et al. in *Br. J. Anaesth.* (1989) 62:213–215). Thus the observed bradycardia is unpredictable and the success or failure of one cyclodextrin-propofol combination does not predict the results that would be obtained with the success or failure of another cyclodextrin-propofol combination.

In a more recent study, the complexation of propofol with HP-β-CD was studied by physicochemical methods, nuclear magnetic resonance, spectroscopic methods, and by a comparison of the anesthetic properties in rats of the uncomplexed propofol (Diprivan® emulsion-type formulation) to that of the complexed propofol (G. Trapani et al. in *J. Pharm. Sci.* (1998), 87(4):514–518). Trapani et al. determined there are significant differences between the two formulations in the induction time and sleeping time. In the field of generic drugs where bioequivalence between a currently approved product and a generic product is necessary, the HP-β-CD/propofol formulation could not be approved due to the lack of bioequivalence. They suggested the possibility that the rats did not feel pain on injection but provided no data to support the suggestion.

International Publication No. WO 96/32135 to FARMARC et al. discloses parenteral and enema formulations comprising propofol and HP-β-CD. FARMARC et al. state that the preferred molar ratio of propofol to HP-CD is about 1:2 to about 1:2.5 (which corresponds to a 1:15.75 to 1:19.65 wt./wt. ratio) in the absence of a cosolvent in order to obtain a clear colorless solution. The ratio can be reduced to 1.5 to <2.0 (which corresponds to a 1:11.79 to 1:15.75 wt./wt. ratio) if a cosolvent (such as glycol, propylene glycol, or polyethylene glycol) is added. FARMARC et al. also state that propofol concentrations of only up to 30 mg/mL can be achieved; however, they recognize that the toxic properties of HP-β-CD limits the practical concentration of HP-CD to 215 mg/mL. Accordingly, the art recognizes the undesired toxicity of HP-β-CD based formulations of propofol.

A sulfobutyl ether derivative (SBE-β-CD), in particular the derivative with an average of about 7 substituents per cyclodextrin molecule, is being commercialized by CyDex, Inc. as CAPTISOL®. The anionic sulfobutyl ether substituent dramatically improves the aqueous solubility of the parent cyclodextrin. In addition, the presence of the charges decreases the ability of the molecule to complex with cholesterol as compared to the hydroxypropyl derivative.

Reversible, non-covalent, complexation of

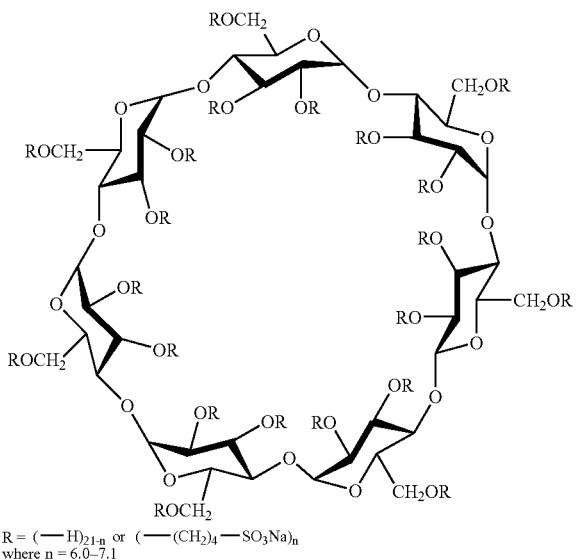

R = (—H)$_{21-n}$ or (—(CH$_2$)$_4$—SO$_3$Na)$_n$
where n = 6.0–7.1

Sulfobutyl Ether-β-Cyclodextrin (Captisol®) drugs with CAPTISOL® cyclodextrin generally allows for increased solubility and stability of drugs in aqueous solutions. While CAPTISOL® cyclodextrin is a relatively new but known cyclodextrin, its combined use with propofol in parenteral formulations and its effect upon the behavior of propofol when administered parenterally has not previously been evaluated.

The safety of cyclodextrins is often compared by way of in-vitro hemolysis studies. As depicted in FIG. 1 (Thompson, D. O., *Critical Reviews in Therapeutic Drug Carrier Systems*, (1997), 14(1), 1–104), the hemolytic behavior of the CAPTISOL® cyclodextrin is compared to the same for the parent β-cyclodextrin, the commercially available hydroxypropyl derivatives, ENCAPSIN™ cyclodextrin (degree of substitution3–4) and MOLECUSOL® cyclodextrin (degree of substitution~7–8), and two other sulfobutyl ether derivatives, SBE1-β-CD and SBE4-β-CD. Unlike the other cyclodextrin derivatives, SAE-CD derivatives, in particular those such as the CAPTISOL® cyclodextrin (degree of substitution~7) and SBE4-β-CD (degree of substitution~4), show essentially no hemolytic behavior in concentrations typically used to solubilize pharmaceutical formulations. These SAE-CDs exhibit substantially lower membrane damaging potential than the commercially available hydroxypropyl derivatives.

Sulfated cyclodextrin derivatives have also been prepared and their effects on blood lotting time evaluated. Sulfated cyclodextrins were found to interfere significantly with blood clotting time, especially when compared to the sulfoalkyl ether cyclodextrins (Thompson, D. O., *Critical Reviews in Therapeutic Drug Carrier Systems*, (1997), 14(1), 1–104).

Methylated cyclodextrins have been prepared and their hemolytic effect on human erythrocytes has been evaluated. These cyclodextrins were found to cause moderate to severe hemolysis (Jodal et al., *Proc. 4$^{th}$ Int. Symp. Cyclodextrins*, (1988), 421–425; Yoshida et al., *Int. J Pharm.*, (1988), 46(3), 217–222).

The osmolality of a formulation is generally associated with its hemolytic potential: the higher the osmolality (or the more hypertonic), the greater the hemolytic potential. Zannou et al. ("Osmotic properties of sulfobutyl ether and hydroxypropyl cyclodextrins", *Pharma Res.* (2001), 18(8),) compared the osmolality of solutions containing SBE-CD and HP-CD. As depicted in FIG. 2, the SBE-CD containing solutions have a greater osmolality than HP-CD containing solutions comprising similar concentrations of cyclodextrin derivative.

Of the different cyclodextrins mentioned above, the sulfoalkyl ether cyclodextrins are most suitable for parenteral administration.

Thus, in the field of sedative hypnotic therapy, there remains the need for improved injectable formulations that have a reduced or eliminated incidence of pain upon injection, enhanced stability, minimal potential for allergic reaction and microbial growth, and/or minimal cardiac side effects caused by the formulation.

SUMMARY OF THE INVENTION

The present invention seeks to overcome the disadvantages present in known formulations. As such, a sulfoalkyl ether cyclodextrin (SAE-CD)-based parenteral formulations of a sedative hypnotic, such as propofol, is provided. The present formulation can provide reduced pain on injection as compared to commercially available emulsion-type formulations. In addition, the present formulation is pharmaceutically stable and has a reduced potential for bacterial contamination, allergic reaction to the formulation components, and hyperlipidemia in recipients as compared to commercially available emulsion-type formulations of propofol. The present formulation may provide enhanced photochemical stability of propofol over the commercially available Diprivan® formulation. Unlike the HP-β-CD based formulation, the present liquid formulation does not induce substantial bradycardia or hemolysis when administered by injection. Moreover, the present formulation possesses other physicochemical advantages over the HP-β-CD based formulation.

An SAE-CD-containing formulation can be prepared with sufficient propofol solubility and stability for a commercial product. The SAE-CD-containing formulation of propofol can be prepared as a clear aqueous true solution that can be sterile filtered through a filter of pore sizes 0.45 microns or less and is stable under a variety of storage conditions. The SAE-CD-containing liquid formulation can also be converted to a solid or powder for reconstitution.

One aspect of the invention provides a liquid formulation comprising a therapeutically effective amount of a sedative hypnotic agent, such as propofol, and a sulfoalkyl ether cyclodextrin present in an amount sufficient to reduce the pain on injection typically associated with the parenteral administration of a propofol emulsion-type formulation. The SAE-CD can be present in less than stoichiometric, stoichiometric or greater than stoichiometric amounts with respect to the amount of propofol present in the formulation.

Specific embodiments of the invention include those wherein: 1) the propofol to SAE-CD molar ratio is less than one, about one or greater than one; 2) the SAE-CD is sulfobutyl ether 4-β-CD or sulfobutyl ether 7-β-CD; 3) the SAE-CD is a compound of the formula 1 or a mixture thereof; 4) the liquid formulation further comprises a preservative, an antioxidant, a buffering agent, an acidifying agent, a solubilizing agent, a complexation enhancing agent, saline, an electrolyte, another therapeutic agent, an alkalizing agent, an antimicrobial agent, an antifungal agent or a combination thereof; 5) the SAE-CD is present in an amount sufficient to provide a clear solution; 6) the sedative hypnotic agent is propofol; and/or 7) the liquid formulation is lyophilized or otherwise dried to form a solid formulation for reconstitution.

The invention also provides a liquid formulation of propofol that can be sterile filtered, wherein the formulation comprises a liquid carryier, an SAE-CD and propofol. Another aspect of the invention provides a method of reducing or eliminating the pain on injection typically associated with the parenteral administration of a propofol-containing liquid comprising the step of administering a liquid formulation comprising a sulfoalkyl ether cyclodextrin and propofol.

The invention also provides a method of administering a sedative hypnotic agent comprising the step of administering a liquid formulation comprising a sulfoalkyl ether cyclodextrin and a sedative hypnotic agent, such as propofol.

Another aspect of the invention provides a method of inducing hypnosis or a method of inducing or maintaining sedation in a mammal comprising the step of administering a liquid formulation comprising an SAE-CD and a sedative hypnotic agent, such as propofol, while reducing the pain on injection typically associated with the administration of sedative hypnotic emulsion-type formulations.

Specific embodiments of the methods of the invention include those wherein: 1) the sedative hypnotic agent is propofol; 2) the method further comprises the step of administering the liquid formulation by injection, infusion, or orally; 3) the method further comprises the step of mixing the SAE-CD and propofol, and optionally one or more other ingredients, in a solution to form the liquid formulation; 4) the liquid formulation comprises an excess, on a molar basis, of SAE-CD; 5) the liquid formulation comprises an excess, on a molar basis, of sedative hypnotic agent; 6) the liquid formulation does not cause bradycardia in a subject being administered the liquid formulation; 7) the reduced pain on injection is based upon a comparison to the commercially available Diprivan® emulsion-type formulation; 8) the liquid formulation causes less or no bradycardia in a subject being administered the liquid formulation as compared to a comparable formulation containing hydroxypropyl β-cyclodextrin and a sedative hypnotic agent; 9) the liquid formulation provides a heart-rate response similar to that of DIPRIVAN® emulsion-type formulation; 10) the liquid formulation provides a cardiac output response similar to that of DIPRIVAN® emulsion-type formulation; 11) the liquid formulation provides a blood pressure response similar to that of DIPRIVAN® emulsion-type formulation; 12) the liquid formulation provides a electroencephalographic response similar to that of DIPRIVAN® emulsion-type formulation; 13) the liquid formulation provides pharmacokinetics similar to that of DIPRIVAN® emulsion-type formulation; 14) the liquid formulation provides pharmacodynamics similar to that of DIPRIVAN® emulsion-type formulation; 15) the liquid formulation provides equivalent or improved chemical stability of propofol as compared to DIPRIVAN® emulsion-type formulation; 16) the liquid formulation can be converted to a solid formulation for reconstitution; 17) the solid formulation provides equivalent or improved chemical stability of propofol as compared to DIPRIVAN® emulsion-type formulation; and 18) the liquid formulation demonstrates a reduced potential to support microbial growth as compared to DIPRIVAN® and Propofol Injectable Emulsion.

The invention also provides methods of preparing a sedative hypnotic-based liquid formulation. A first method comprises the steps of: forming a first aqueous solution comprising SAE-CD; forming a second solution comprising propofol; and mixing the first and second solutions to form the liquid formulation. A second method is similar to the first step except that the propofol is added directly to the first solution without formation of the second solution. A third method is similar to the first except that the SAE-CD is added directly to the second solution without formation of the first solution. A fourth method comprises the steps of: adding a solution comprising propofol to a powdered or particulate SAE-CD. A fifth method comprises the steps of: adding the propofol directly to the powdered or particulate SAE-CD; and adding a second solution. A sixth method comprises the steps of: creating the liquid formulation by any of the above methods and then isolating a solid material by lyophilization, spray-drying, spray-freeze-drying, anti-solvent precipitation, a process utilizing a supercritical or near supercritical fluid, or other methods known to those of ordinary skill in the art to make a powder.

Specific embodiments of the methods of preparing the liquid formulation include those wherein: 1) the method further comprises the step of sterile filtering the formulation through a filtration medium having a pore size of 0.1 microns or larger; 2) the liquid formulation is sterilized by irradiation or autoclaving; 3) the method further comprises the step of isolating a powder from the solution; 4) the solution is purged with nitrogen or argon or other inert pharmaceutically acceptable gas such that a substantial portion of the oxygen dissolved in the solution is removed.

Another aspect of the invention provides a kit comprising: a first pharmaceutical composition comprising an SAE-CD and a second pharmaceutical composition comprising a sedative hypnotic agent. The first and second formulations can be mixed and formulated as a liquid dosage form prior to administration to a subject. Either one or both of the first and second pharmaceutical compositions can comprise additional pharmaceutical excipients.

Specific embodiments of the kit include those wherein: 1) the first and second pharmaceutical compositions are provided in separate containers or in separate chambers of a container having two or more chambers; 2) the kit further comprises a pharmaceutically acceptable liquid carrier used to suspend and dissolve the first and/or second pharmaceutical compositions; 3) the liquid carrier is included with the first and/or second pharmaceutical composition; 4) the liquid carrier is provided in a container or chamber separate from the first and second pharmaceutical compositions; 5) the first and/or second pharmaceutical composition and/or liquid carrier further comprises a preservative, an antioxidant, a buffering agent, an acidifying agent, saline, an electrolyte, another therapeutic agent, an alkalizing agent, an antimicrobial agent, an antifungal agent, a solubility enhancing agent or a combination thereof; 6) the kit is provided chilled; 7) the liquid carrier and/or chamber has been purged with a pharmaceutically acceptable inert gas to remove substantially all of the oxygen dissolved in the liquid carrier; 8) the chambers are substantially free from oxygen. Still another aspect of the invention provides a reconstitutable solid pharmaceutical composition comprising a sedative hypnotic agent, an SAE-CD and optionally at least one other pharmaceutical excipient. When this composition is reconstituted with an aqueous liquid to form a liquid formulation it can be administered by injection, infusion, or orally to a subject. The liquid formulation so formed can provide reduced pain on injection as compared to emulsion-type formulations containing a sedative hypnotic.

Specific embodiments of the reconstitutable solid pharmaceutical composition includes those wherein: 1) the composition comprises an admixture of a solid SAE-CD and sedative hypnotic-containing solid comprising a sedative hypnotic and optionally at least one solid pharmaceutical excipient, such that a major portion of the sedative hypnotic is not complexed with the SAE-CD prior to reconstitution; and/or 2) the composition comprises a solid mixture of an SAE-CD and a sedative hypnotic, wherein a major portion of the sedative hypnotic is complexed with the SAE-CD prior to reconstitution.

Yet another aspect of the invention provides a pharmaceutical kit comprising a first container containing a liquid vehicle and a second container containing a reconstitutable solid pharmaceutical composition comprising an SAE-CD and a sedative hypnotic.

Specific embodiments of this kit include those wherein: 1) the liquid vehicle comprises an aqueous liquid carrier; 2) the composition comprises an admixture of a solid SAE-CD and sedative hypnotic-containing solid comprising a sedative hypnotic and optionally at least one solid pharmaceutical excipient, such that a major portion of the sedative hypnotic is not complexed with the SAE-CD prior to reconstitution; and/or 3) the composition comprises a solid mixture of an SAE-CD and a sedative hypnotic, wherein a major portion of the sedative hypnotic is complexed with the SAE-CD prior to reconstitution.

These and other aspects of this invention will be apparent upon reference to the following detailed description, examples, claims and attached figures.

BRIEF DESCRIPTION OF THE FIGURES

The following drawings are given by way of illustration only, and thus are not intended to limit the scope of the present invention.

DETAILED DESCRIPTION OF THE INVENTION

A formulation comprising an SAE-CD and propofol provides unexpected advantages over other formulations comprising propofol and another cyclodextrin derivative or organic solvent. With a formulation according to the invention, the degradation of propofol can be essentially eliminated through proper formulation, manufacturing and packaging. The effects of antioxidants, presence of oxygen, pH and buffer species on the stability of propofol have all been evaluated in controlled testing under real time and accelerated conditions. Moreover, the presently claimed formulation overcomes many of the undesired properties of other known formulations while at the same time providing a formulation that is bioequivalent with the currently FDA approved emulsion-type formulation.

The liquid formulation of the invention is generally not an emulsion-type formulation; however, the present invention also includes emulsion-type formulations containing a sedative hypnotic agent and an SAE-CD, wherein the formulation possesses pharmacological and/or physicochemical advantages as compared to a comparable emulsion formulation not containing the SAE-CD.

Figure 1:
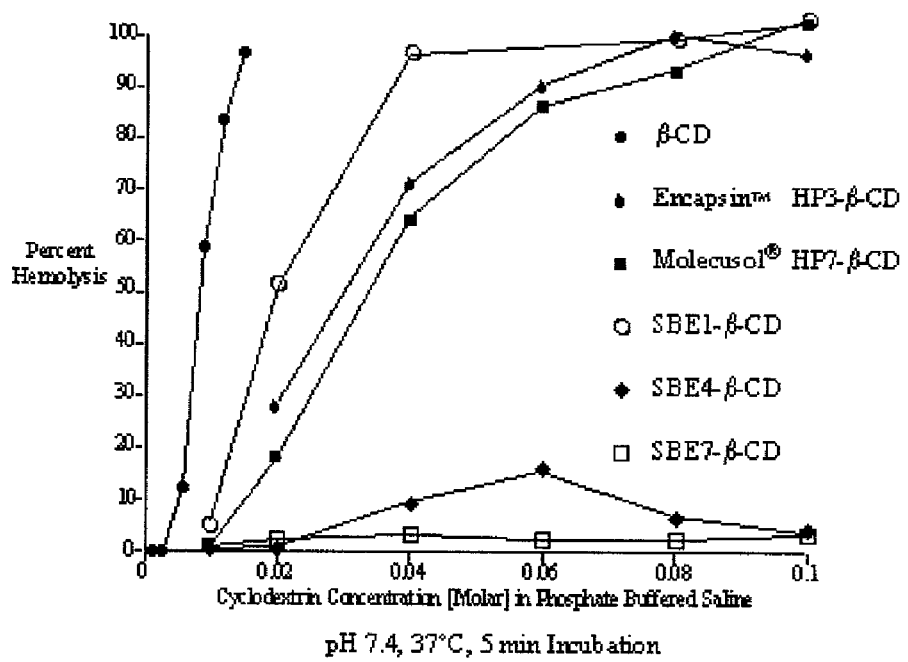
FIG. 1 depicts a prior art graph showing the hemolytic potential for various different cyclodextrin derivatives.
Figure 2:
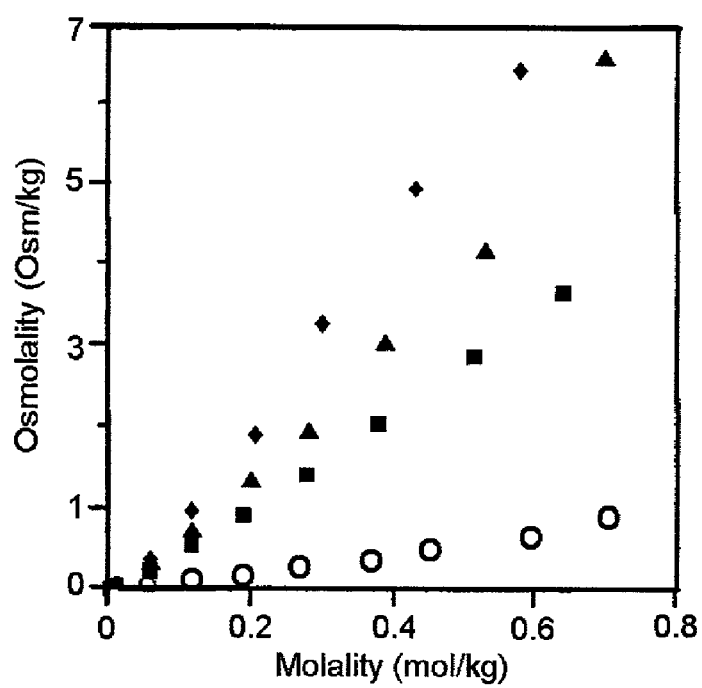
FIG. 2 depicts a graph of the osmolality versus molality of SBE-CD containing solutions (■—SBE4-β-CD; ♦—SBE9-β-CD; ▲—SBE7-β-CD) and HP-β-CD containing solutions (○).

As detailed above in reference to FIG. 1, the safety of cyclodextrins is often compared by way of in-vitro hemolysis studies. Unlike the other cyclodextrin derivatives, SAE-CD derivatives, in particular those such as CAPTISOL® (degree of substitution≈7) and SBE4-β-CD (degree of substitution≈4), show essentially no hemolytic behavior in concentrations typically used to solubilize pharmaceutical formulations and exhibit substantially lower membrane damaging potential than the commercially available hydroxypropyl derivatives. Accordingly, the formulations of the present invention cause less hemolysis than other propofol-containing cyclodextrin derivative based formulations and than the DIPRIVAN® emulsion-type formulation.

The present invention provides SAE-CD based parenteral formulations of propofol, wherein the SAE-CD is a compound of the Formula 1:

Formula 1

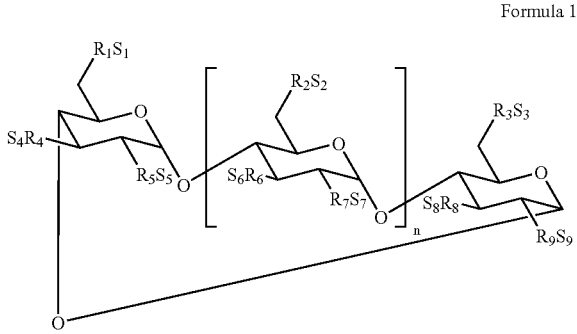

wherein:

n is 4, 5 or 6;

$R_1$, $R_2$, $R_3$, R4, $R_5$, R6, $R_7$, $R_8$ and $R_9$ are each, independently, —O— or a —O—($C_2$–$C_6$ alkylene)—$SO_3^{-3}$ group, wherein at least one of $R_1$ and $R_2$ is independently a —O—($C_2$–$C_6$ alkylene)—$SO_3^-$ group, preferably a —O—$(CH_2)_m SO_3$ group, wherein m is 2 to 6, preferably 2 to 4, (e.g. —$OCH_2CH_2CH_2SO_3^-$ or —$OCH_2CH_2CH_2CH_2SO_3^-$); and $S_1$, $S_2$, $S_3$, $S_4$, $S_5$, $S_6$, $S_7$, $S_8$ and $S_9$ are each, independently, a pharmaceuti cally acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amine cations such as the cations of ($C_1$–$C_6$)-alkylamines, piperidine, pyrazine, ($C_1$–$C_6$)-alkanolamine and ($C_4$–$C_8$)-cycloalkanolamine.

The SAE-CD used in the liquid or solid formulation is described in U.S. Pat. Nos. 5,376,645 and 5,134,127 to Stella et al, the entire disclosures of which are hereby incorporated by reference. The preparation process may comprise dissolving the cyclodextrin in aqueous base at an appropriate temperature, e.g., 70° to 80° C., at the highest concentration possible. For example, to prepare the cyclodextrin derivatives herein, an amount of an appropriate alkyl sultone, corresponding to the number of moles of primary CD hydroxyl group present, is added with vigorous stirring to ensure maximal contact of the heterogeneous phase. According to one embodiment, the SAE-CD is SBE-7-β-CD (CAPTISOL®), or SBE-4-β-CD.

The terms "alkylene" and "alkyl," as used herein (e.g., in the -0-($C_2$–$C_6$-alkylene)$SO_3^-$ group or in the alkylamines), include linear, cyclic, and branched, saturated and unsaturated (i.e., containing one double bond) divalent alkylene groups and monovalent alkyl groups, respectively. The term "alkanol" in this text likewise includes both linear, cyclic and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

The present invention provides compositions containing a mixture of cyclodextrin derivatives, having the structure set out in formula (I), where the composition overall contains on the average at least 1 and up to 3n+6 alkylsulfonic acid moieties per cyclodextrin molecule. The present invention also provides compositions containing a single type of cyclodextrin derivative, or at least 50% of a single type of cyclodextrin derivative.

The cyclodextrin derivatives of the present invention are obtained as purified compositions, i.e., compositions containing at least 95 wt. % of cyclodextrin derivative(s). In a preferred embodiment, purified compositions containing at least 98 wt. % cyclodextrin derivative(s) are obtained.

In some of the compositions of the invention unreacted cyclodextrin has been substantially removed, with the remaining impurities (i.e., <5 wt. % of composition) being inconsequential to the performance of the cyclodextrin derivative-containing composition.

Exemplary SAE-CD derivatives include SBE4-β-CD, SBE7-β-CD, SBE11-β-CD, and SBE4-γ-CD which correspond to SAE-CD derivatives of the formula I wherein n=5, 5, 5 and 6; m is 4; and there are 4, 7, 11 and 4 sulfoalkyl ether substituents present, respectively. It has been found that these SAE-CD derivatives increase the solubility of poorly water soluble sedative hypnotic drugs, especially propofol, to varying degrees.

By "therapeutic agent/SAE-CD complex" is generally meant a clathrate or inclusion complex of a sulfoalkyl ether cyclodextrin derivative of the formula (1) and a therapeutic agent. The ratio of therapeutic agent:SAE-CD present in the complex can vary and can be in the range of about 1:2 to about 2:1, on a molar basis, respectively, and preferably about 1:1. In another embodiment of the dosage forms described herein, the ratio of therapeutic agent: SAE-CD is in the range of about 2:1 to about 1:100 on a molar basis, preferably about 1:1 to about 1:20 and more preferably about 1:1 to about 1:10 on a molar basis. Thus, the SAE-CD will generally be, but need not be, present in excess of the therapeutic agent. The amount of excess will be determined by the intrinsic solubility of the agent, the expected dose of the agent, and the binding constant for inclusion complexation between the specific drug (agent) and the specific SAE-CD.

By "complexed" is meant "being part of a clathrate or inclusion complex with", i.e., a complexed therapeutic agent is part of a clathrate or inclusion complex with a sulfoalkyl ether cyclodextrin derivative. By "major portion" is meant at least about 50% by weight of the therapeutic compound. Thus, a formulation according to the present invention will contain a therapeutic agent of which more than about 50% by weight is complexed with an SAE-CD. In various embodiments, preferably greater than 60% by weight, more preferably greater than 75% by weight, even more preferably greater than 90% by weight, and most preferably greater than 95% by weight of the therapeutic agent will remain complexed with an SAE-CD while in the pharmaceutical formulation. The actual percent of drug that is complexed will vary according to the complexation equilibrium constant characterizing the complexation of a specific SAE-CD to a specific drug. It should be noted that an SAE-CD can form one or more ionic bonds with a positively charged compound.

Figure 5:
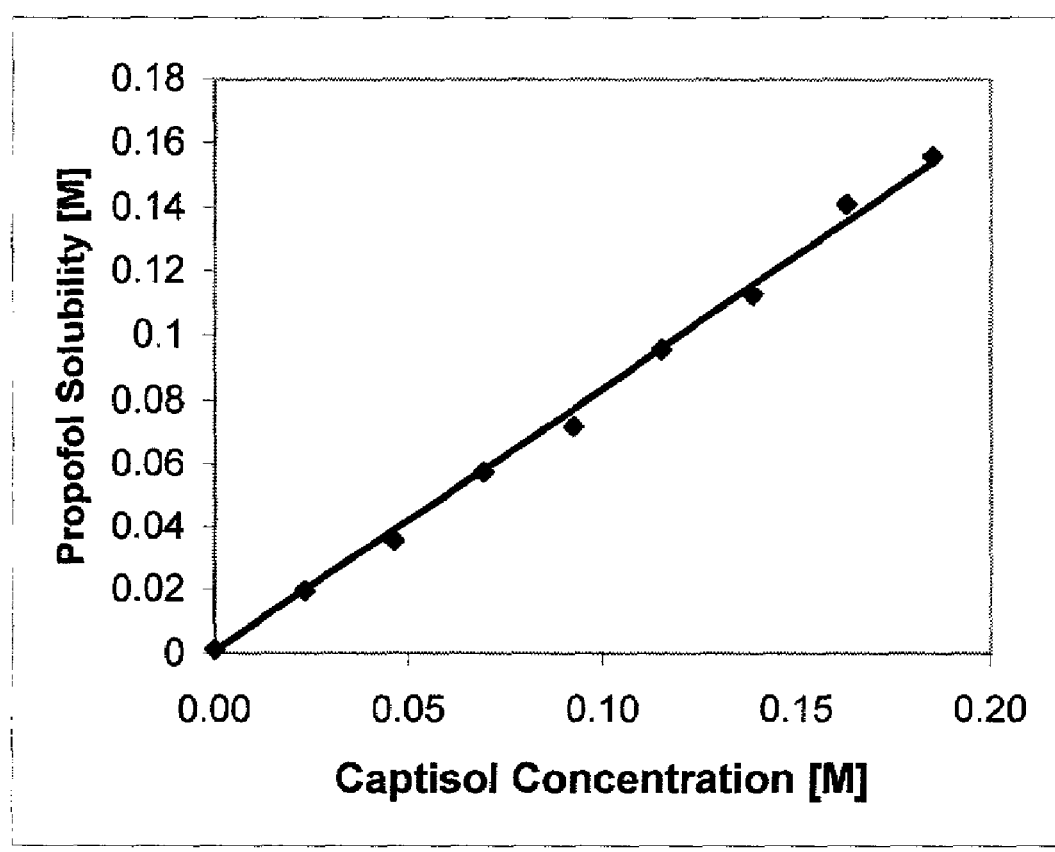
FIG. 5 depicts a phase solubility diagram (25° C.) for propofol in solutions containing the CAPTISOL® cyclodextrin.

Propofol has a solubility of about 0.15 mg/mL in water. FIG. 5 depicts a phase solubility diagram for propofol and SBE7-β-CD in unbuffered water. The slope of the line can be used to determine the binding constant of SBE7-β-CD for propofol. The calculated binding constant is about 3800 to 4800M$^{-1}$ (25° C.) as determined by the equilibrium solubility technique (T. Higuchi et al. in "Advances in Analytical Chemistry and Instrumentation Vol. 4"; C. N. Reilly ed.; John Wiley & Sons, Inc, 1965, pp. 117–212). The binding constant is almost invariant within the temperature range of 5 to 40° C. This binding constant is not dependent upon the pH of the solution at pH values below about 9.5.

To raise the aqueous concentration of propofol from its solubility of 0.15 mg/mL to the required formulation concentration of 10 mg/mL requires a 15% w/v solution of CAPTISOL® cyclodextrin. Allowing for a 10% deviation (as might occur during manufacture) in either CAPTISOL® cyclodextrin or propofol concentration generally requires a CAPTISOL® cyclodextrin concentration of approximately 18–20% w/v. This concentration will maintain the propofol in solution under the anticipated extremes of environmental and manufacturing conditions.

At CAPTISOL® cyclodextrin concentrations above 15% w/v, the equilibrium process of Equations 1 and 2 are shifted to the formation of more complex. At a fixed total concentration of propofol, this serves to decrease the concentration of free (uncomplexed) propofol.

Generally, the greater the percentage of drug that is complexed, the more effectively the SAE-CD will reduce pain on injection. It should be understood that the degree to which pain on injection is reduced may vary according to the site of injection. Accordingly, a greater reduction of pain on injection may be expected when the injection site is the arm and a smaller reduction of pain on injection may be expected when the injection site is the back of the hand. Transient local pain can be minimized if larger veins of the forearm or anticubital fossa are used (DIPRIVAN® Injectable Emulsion Propofol, Professional Information Brochure, Zeneca Pharmaceuticals, April 2001).

The ratio of sedative hypnotic agent:SAE-CD present in the formulation will depend on a number of factors, such as, the intrinsic solubility of the agent, the expected dose of the agent, and the binding constant for inclusion complexation between the specific drug (agent) and the specific SAE-CD. These factors combined will determine the amount of SAE-CD needed in the dosage form and therefore the ratio of SAE-CD: therapeutic agent.

Generally, the amount of each ingredient in a pharmaceutical formulation falls within a predetermined range. If a ±10% variation in propofol concentration is allowed during manufacturing, there might be occasion where the propofol concentration is 11 mg/mL or 0.0617 M. Assuming also the lower complexation constant of 3800 M$^{-1}$, then the minimum amount of CAPTISOL® cyclodextrin needed in that formulation is 159 mg/mL or 0.073M. This formulation would have a CAPTISOL® cyclodextrin/propofol mole ratio of about 1.19:1. If we set this as the lower limit of the CAPTISOL® cyclodextrin concentration (90% limit, again assuming a potential ±10% variation), then the target CAPTISOL® cyclodextrin concentration would be about 176 mg/mL (100%) and the 110% limit would be about 194 mg/mL (0.0897 M). On the other hand, if the CAPTISOL® cyclodextrin concentration was on the high side at 0.0897 M and propofol was on the low side (90% or 9 mg/mL) at 0.05 M, the molar ratio would be about 1.77:1 (CAPTISOL® cyclodextrin to propofol). A ratio higher than this might lead to less pain on injection by complexing more of the free propofol.

Accordingly, the generally minimum effective CAPTISOL® cyclodextrin/propofol molar ratio is about 1.1: 1, based upon the complexation constants above. Minimizing the amount of free propofol present in the formulation may result in a formulation exhibiting a reduced pain on injection as compared to another known formulation. Therefore, a higher SAE-CD/propofol ratio may be required based upon the pain on injection observed when the formulation is administered. For example, using the binding constant of 3800 M$^{-1}$ and a CAPTISOL cyclodextrin of 14.4% w/v (0.0665M), the concentration of uncomplexed propofol in solution is about 2.21% of the total or 0.00124M. If the concentration of CAPTISOL cyclodextrin is increased to 50% w/v (0.231M), the concentration of uncomplexed propofol drops to about 0.15% of the total or 0.000084M. In this formulation, the CAPTISOL cyclodextrin/propofol molar ratio is about 4.1:1. Generally, the molar ratio will fall between the range of 1:1 to 5:1 CAPTISOL® cyclodextrin/propofol. A ratio in the range of about 1:1 to 2:1 CAPTISOL® cyclodextrin/propofol is also suitable. A ratio in the range of 2.0:1 to 4.8:1 is also suitable for formulations with reduced amounts of uncomplexed propofol.

It should be understood that other SAE-CD compounds of the formula 1 may be used in the liquid formulation of the invention. These other SAE-CD compounds differ from CAPTISOL® cyclodextrin in their degree of substitution by sulfoalkyl groups, the number of carbons in the sulfoalkyl chain, their molecular weight, the size of the base cyclodextrin used to form the SAE-CD and or their substitution patterns. In addition, the derivatization of β-cyclodextrin with sulfoalkyl groups occurs in a controlled, although not exact manner. For this reason, the degree of substitution is actually a number representing the average number of sulfoalkyl groups per cyclodextrin molecule. In addition, the regiochemistry of substitution of the hydroxyl groups of the cyclodextrin is variable with regard to the substitution of specific hydroxyl groups of the hexose ring. For this reason, sulfoalkyl substitution of the different hydroxyl groups is likely to occur during manufacture of the SAE-CD, and a particular SAE-CD will possess a preferential, although not exclusive or specific, substitution pattern. Given the above, the molecular weight of a particular SAE-CD may vary from batch to batch and will vary from SAE-CD to SAE-CD. All of these variations can lead to changes in the complexation equilibrium constant $K_b$ which in turn will affect the required ratio of SAE-CD to propofol. The complexation constant is also somewhat variable with temperature and allowances in the ratio are required such that the agent remains solubilized during the temperature fluctuations that can occur during manufacture, storage, transport and use. Accordingly, the molar ratio of SAE-CD/propofol may vary within the range of about 1:1 to about 10:1, or about 1:1 to about 6.2:1.

Unlike HP-β-CD that can practically provide a liquid formulation comprising propofol concentration of only 30 mg/mL, the present SAE-CD based formulation can provide a liquid formulation comprising greater than 55 mg/mL.

Figure 3:
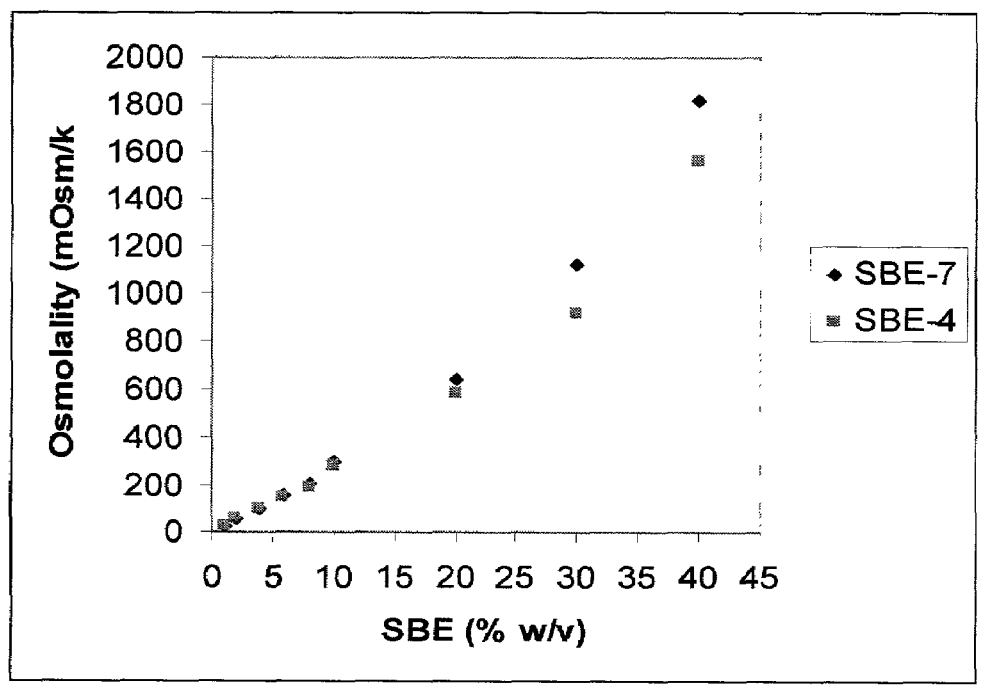
FIG. 3 depicts a graph of the osmolality versus concentration of SBE-CD in an aqueous solution.

FIG. 3 depicts the relationship between osmolality and concentration of SBE-CD in an unbuffered aqueous solution at room temperature. At concentrations up to about 20% to 30% w/v, the relationship is linear. At SBE-CD concentrations of 14% to 22% w/v, suitable for dissolution of propofol, the solution is hypertonic in the range of about 220 to 740 mOsm/kg.

Figure 4:
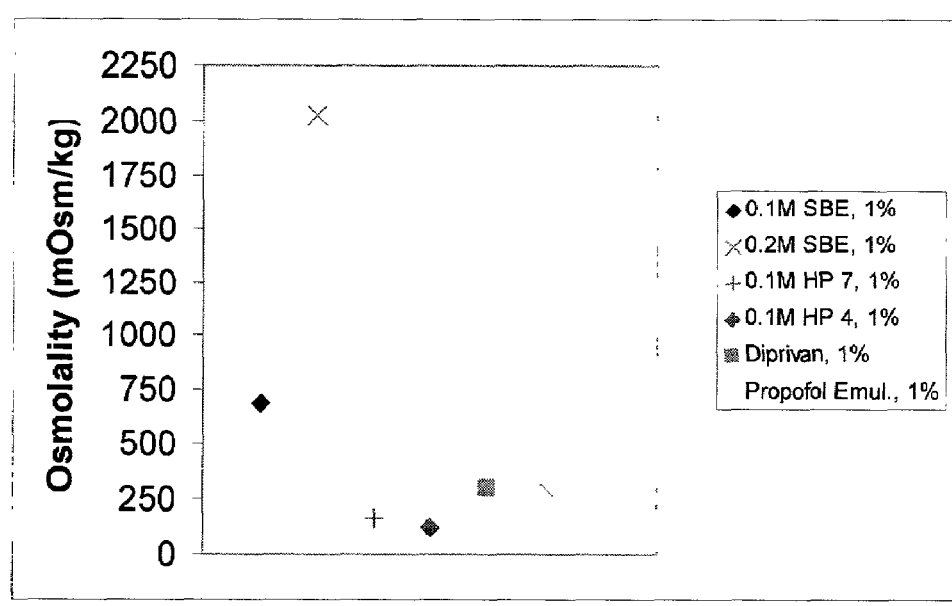
FIG. 4 depicts the osmolality of various cyclodextrin derivate-containing aqueous solutions comprising 1% w/v propofol.

FIG. 4 depicts the osmolality of solutions containing 1% wt. propofol in the presence of known concentrations of cyclodextrin derivatives as compared to the DIPRIVAN® formulation and the propofol emulsion formulation of BAXTER. The cyclodextrin derivatives include SBE7-β-CD, HP7-β-CD, and HP4-β-CD. The DIPRIVAN® formulation and the BAXTER propofol emulsion formulation are isotonic. The BAXTER formulation comprises propofol (1% wt.), soybean oil (100 mg/mL), glycerol (22.5 mg/mL), egg yolk phospholipid (12 mg/mL), and sodium metabisulfite (0.25 mg/mL). At similar concentrations, the hydroxypropyl cyclodextrin derivatives have a three to four fold lower osmolality than the sulfobutyl ether cyclodextrin. However, contrary to the teaching of the art, the SAE-CD solutions induce less hemolysis than comparable HP-β-CD solutions (FIG. 1) even though the SAE-CD has a higher osmolality than the HP-β-CD.

Hemolytic assays are generally used in the field of parenteral formulations to predict whether or not a particular formulation is likely to be unsuitable for injection into the bloodstream of a subject. If the formulation being tested induces a significant amount of hemolysis, that formulation will generally be considered unsuitable for administration to a subject. All of the SAE-CD compounds of the invention induce less hemolysis than β-cyclodextrin, and all of the preferred SAE-CD compounds tested induce less hemolysis than HP-β-CD. Accordingly, the invention also provides a liquid formulation of a sedative hypnotic agent, wherein the formulation has a reduced hemolytic potential as compared to other cyclodextrin-based formulations.

A formulation containing 22% w/v CAPTISOL® cyclodextrin, and 10 mg/mL propofol in water was compared to DIPRIVAN® emulsion-type formulation and to a formulation containing only 22% w/v CAPTISOL® cyclodextrin in water. The formulations were evaluated for their potential to cause visual hemolysis when incubated with whole blood for approximately 5 minutes at approximately 37° C. at each of ten different formulation:whole blood concentration ratios, ranging from 1:1 v:v to 0.001:1 v/v. The DIPRIVAN® formulation induced moderate hemolysis at concentration ratios of 1:1 and slight hemolysis at concentration ratios of 0.5:1, 0.25:1 and 0.1:1. The CAPTISOL® formulation in water and the CAPTISOL® formulation of propofol each showed no indication of hemolysis at each of the 10 concentration ratios tested.

The pig is used in assays designed to determine the efficacy or safety of drug formulations, particularly when cardiovascular function is being evaluated. A formulation prepared according to the present disclosure and containing CAPTISOL® cyclodextrin, propofol and water was administered to pigs by intravenous injection. The effects of the formulation upon cardiovascular function (i.e. heart-rate, cardiac output, and mean arterial pressure) was compared to that of DIPRIVAN® emulsion-type formulation. The results of the study indicated that the liquid formulation of the present invention and the DIPRIVAN® formulation were equivalent in their effects on cardiovascular function. In the same study, the electroencephalographic response was also measured. The liquid formulation of the invention provided an electroencephalographic response comparable to that of the DIPRIVAN® emulsion-type formulation.

The invention also includes a method of reducing pain on injection for an emulsion-type formulation of a sedative hypnotic formulation such as DIPRIVAN® emulsion-type formulation. In this embodiment, the SAE-CD is included in the emulsion formulation to bind or complex with dissolved sedative hypnotic and thereby reduce the pain on injection when the emulsion is administered to a subject. The formulation maintains its state as an emulsion even though the SAE-CD is present.

The liquid formulation of the invention may also be converted to a solid formulation for reconstitution. A reconstitutable solid pharmaceutical composition according to the invention comprises a sedative hypnotic agent, an SAE-CD and optionally at least one other pharmaceutical excipient. This composition is reconstituted with an aqueous liquid to form a liquid formulation that is administered by injection, infusion, or orally to a subject. The composition can comprise an admixture of a solid SAE-CD and a sedative hypnotic agent-containing solid comprising a sedative hypnotic agent and optionally at least one solid pharmaceutical excipient, such that a major portion of the sedative hypnotic agent is not complexed with the SAE-CD prior to reconstitution. Alternatively, the composition can comprise a solid mixture of an SAE-CD and a sedative hypnotic agent, wherein a major portion of the sedative hypnotic is complexed with the SAE-CD prior to reconstitution.

The reconstitutable formulation is prepared according to any of the following processes. A liquid formulation of the invention is first prepared, then a solid is formed by lyophilization (freeze-drying), spray-drying, spray freeze-drying, antisolvent precipitation, various processes utilizing supercritical or near supercritical fluids, or other methods known to those of ordinary skill in the art to make a powder.

The liquid formulation used in the preparation of the solid formulation, may be prepared as described for the liquid formulation of the invention. It may also be prepared to contain an SAE-CD and the sedative hypnotic agent at concentrations greater than typically used in the liquid formulation of the invention, while maintaining the same SAE-CD: sedative hypnotic agent ratio. The greater concentrations can facilitate several of the processes for isolation of the solid formulation.

The invention also provides a pharmaceutical kit comprising a first container containing a liquid vehicle and a second container containing a reconstitutable solid pharmaceutical composition as described above. The liquid vehicle comprises an aqueous liquid carrier such as water, aqueous alcohol, or aqueous organic solvent.

A solubility-enhancing agent can be added to the aqueous liquid formulation of the invention. A solubility-enhancing agent is a compound, or compounds, that enhance(s) the solubility of the propofol in the liquid formulation. When such an agent is present, the ratio of CAPTISOL® cyclodextrin/propofol can be changed. Suitable solubility enhancing agents include one or more organic solvents, detergents, soaps, surfactant and other organic compounds typically used in parenteral formulations to enhance the solubility of a particular agent.

Suitable organic solvents include, for example, ethanol, glycerin, polyethylene glycols, propylene glycol, poloxomers, and others known to those of ordinary skill in the art.

The propofol is generally present in amounts ranging from about 0.1% to 5% by weight or more preferably 1% to 2% by wt. of propofol based upon the total weight of the formulation.

Dosage levels of propofol for producing general anesthesia, both induction (for example about 2.0–2.5 mg/kg of body weight for an adult) and maintenance (for example about 4–12 mg/kg of body weight/hr), and for producing a sedative effect (for example, 0.3–4.5 mg/kg of body weight/hr), may be derived from the substantial literature on propofol. Furthermore, the anesthetist and/or physician would modify the dose to achieve the desired effect in a patient in accordance with the conventional skill in the art.

Soaps and synthetic detergents may be employed as surfactants and as vehicles for detergent compositions. Suitable detergents include cationic detergents and surfactants, for example, polyamines and their salts, quaternary ammonium salts, and amine oxides, alkyl dimethyl substituted halides, dimethyl dialkyl ammonium halides, dimethyl substituted benzene-methanaminium halides, dodecyltrimethylammonium halides, trimethyltetradecylammonium halides, hexadecyltrimethylammonium halides, alkyl pyridinium halides, and alkylamine acetates; anionic detergents and surfactants for example, sulfonic acid salts, alcohol sulfates, alkylbenzene sulfonates, phosphoric acid esters, and carboxylic acid salts, sodium lauryl sulfate, alkyl, aryl, and olefin sulfonates, alkyl olefin, ether and monoglyceride sulfates, and sulfosuccinates; nonionic surfactants and detergents, for example, polyoxyethylenated alkylphenols, alcohol ethoxylates, alkylphenol ethoxylates, and alkanolamides, fatty amine oxides, fatty acid alkanolamides, and poly(oxyethylene)-block-poly(oxypropylene) copolymers, glycerol monooleate, polysorbate 20, polysorbate 21, polysorbate 40, polysorbate 60, polysorbate 61, polysorbate 65, polysorbate 80, polysorbate 81, polysorbate 85, polysorbate 120, polyvinyl alcohols, and sorbitan esters; amphoteric detergents, for example, alkyl β-aminopropionates, and 2-alkylimidazoline quaternary ammonium salts; synthetic or naturally occurring phosphatide; others known to those of ordinary skill in the art; and combinations thereof.

Suitable soaps include fatty acid alkali metal, ammonium, triethanolamine salts and others known to those of ordinary skill in the art.

The dosage form of the invention can also include oils, for example, fixed oils, such as peanut oil, sesame oil, cottonseed oil, corn oil and olive oil; fatty acids, such as oleic acid, stearic acid and isostearic acid; and fatty acid esters, such as ethyl oleate, isopropyl myristate, fatty acid glycerides and acetylated fatty acid glycerides. It can also include alcohols, such as ethanol, isopropanol, hexadecyl alcohol, glycerol and propylene glycol; glycerol ketals, such as 2,2-dimethyl-1,3-dioxolane-4-methanol; ethers, such as poly(ethylene glycol) 450; with petroleum hydrocarbons, such as mineral oil and petrolatum; water; or with mixtures thereof; with or without the addition of a pharmaceutically suitable surfactant, suspending agent or emulsifying agent.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Although not necessary, the formulation of the present invention can include a preservative, antioxidant, buffering agent, acidifying agent, alkalizing agent, antibacterial agent, antifungal agent, solubility enhancing agent, complexation enhancing agent, solvent, electrolyte, salt, water, stabilizer, tonicity modifier, antifoaming agent, oil, emulsifying agent, bulking agent, cryoprotectant or a combination thereof.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, diethanolamine, organic amine base, alkaline amino acids and trolamine and others known to those of ordinary skill in the art.

As used herein, the term "acidifying agent" is intended to mean a compound used to provide an acidic medium for product stability. Such compounds include, by way of example and without limitation, acetic acid, acidic amino acids, citric acid, fumaric acid and other alpha hydroxy acids, hydrochloric acid, ascorbic acid, phosphoric acid, sulfuric acid, tartaric acid and nitric acid and others known to those of ordinary skill in the art.

As used herein, the term "preservative" is intended to mean a compound used to prevent the growth of microorganisms. Such compounds include, by way of example and without limitation, benzalkonium chloride, benzethonium chloride, benzoic acid, benzyl alcohol, cetylpyridinium chloride, chlorobutanol, phenol, phenylethyl alcohol, phenylmercuric nitrate, phenylmercuric acetate, thimerosal, metacresol, myristylgamma picolinium chloride, potassium benzoate, potassium sorbate, sodium benzoate, sodium propionate, sorbic acid, thymol, and methyl, ethyl, propyl or butyl parabens and others known to those of ordinary skill in the art. Particularly useful preservatives include EDTA, pentetate, and combinations thereof.

As used herein, the term "antioxidant" is intended to mean an agent that inhibits oxidation and thus is used to prevent the deterioration of preparations by the oxidative process. Such compounds include, by way of example and without limitation, acetone, potassium metabisulfite, potassium sulfite, ascorbic acid, ascorbyl palmitate, citric acid, butylated hydroxyanisole, butylated hydroxytoluene, hypophosphorous acid, monothioglycerol, propyl gallate, sodium ascorbate, sodium citrate, sodium sulfide, sodium sulfite, sodium bisulfite, sodium formaldehyde sulfoxylate, thioglycolic acid and sodium metabisulfite and others known to those of ordinary skill in the art.

As used herein, the term "buffering agent" is intended to mean a compound used to resist change in pH upon dilution or addition of acid or alkali. Such compounds include, by way of example and without limitation, acetic acid, sodium acetate, adipic acid, benzoic acid, sodium benzoate, citric acid, maleic acid, monobasic sodium phosphate, dibasic sodium phosphate, lactic acid, tartaric acid, potassium metaphosphate, potassium phosphate, monobasic sodium acetate, sodium bicarbonate, sodium tartrate and sodium citrate anhydrous and dihydrate and others known to those of ordinary skill in the art.

A complexation-enhancing agent can be added to the aqueous liquid formulation of the invention. When such an agent is present, the ratio of CAPTISOL® cyclodextrin/propofol can be changed. A complexation enhancing agent is a compound, or compounds, that enhance(s) the complexation of the propofol with the SAE-CD. Suitable complexation enhancing agents include one or more pharmacologically inert water soluble polymers, hydroxy acids, and other organic compounds typically used in liquid formulations to enhance the complexation of a particular agent with cyclodextrins.

Suitable water soluble polymers include water soluble natural polymers, water soluble semisynthetic polymers (such as the water soluble derivatives of cellulose) and water soluble synthetic polymers. The natural polymers include polysaccharides such as inulin, pectins, algin derivatives and agar, and polypeptides such as casein and gelatin, The semi-synthetic polymers include cellulose derivatives such as methylcellulose, hydroxyethyl cellulose, hydroxypropyl cellulose, their mixed ethers such as hydroxypropyl methylcellulose and other mixed ethers such as hydroxyethyl ethylcellulose and hydroxypropyl ethylcellulose, hydroxypropyl methylcellulose phthalate and carboxymethylcellulose and its salts, especially sodium carboxymethylcellulose. The synthetic polymers include polyoxyethylene derivatives (polyethylene glycols) and polyvinyl derivatives (polyvinyl alcohol, polyvinylpyrrolidone and polystyrene sulfonate) and various copolymers of acrylic acid (e.g. carbomer).

Suitable hydroxy acids include by way of example, and without limitation, citric acid, malic acid, lactic acid, and tartaric acid and others known to those of ordinary skill in the art.

As used herein, the term "stabilizer" is intended to mean a compound used to stabilize the therapeutic agent against physical, chemical, or biochemical process which would reduce the therapeutic activity of the agent. Suitable stabilizers include, by way of example and without limitation, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and other known to those of ordinary skill in the art.

As used herein, the term "tonicity modifier" is intended to mean a compound or compounds that can be used to adjust the tonicity of the liquid formulation. Suitable tonicity modifiers include glycerin, lactose, mannitol, dextrose, sodium chloride, sodium sulfate, sorbitol, trehalose and others known to those of ordinary skill in the art. In one embodiment, the tonicity of the liquid formulation approximates the tonicity of blood or plasma.

As used herein, the term "antifoaming agent" is intended to mean a compound or compounds that prevents or reduces the amount of foaming that forms on the surface of the liquid formulation. Suitable antifoaming agents include dimethicone, simethicone, octoxynol and others known to those of ordinary skill in the art.

As used herein, the term "bulking agent" is intended to mean a compound used to add bulk to the lyophilized product and/or assist in the control of the properties of the formulation during lyophilization. Such compounds include, by way of example and without limitation, dextran, trehalose, sucrose, polyvinylpyrrolidone, lactose, inositol, sorbitol, dimethylsulfoxide, glycerol, albumin, calcium lactobionate, and others known to those of ordinary skill in the art.

As used herein, the term "cryoprotectant" is intended to mean a compound used to protect an active therapeutic agent from physical or chemical degradation during lyophilization. Such compounds include, by way of example and without limitation, dimethyl sulfoxide, glycerol, trehalose, propylene glycol, polyethylene glycol, and others known to those of ordinary skill in the art.

As used herein, the term "emulsifier" or "emulsifying agent" is intended to mean a compound added to one or more of the phase components of an emulsion for the purpose of stabilizing the droplets of the internal phase within the external phase. Such compounds include, by way of example and without limitation, lecithin, polyoxylethylene-polyoxypropylene ethers, polyoxylethylene-sorbitan monolaurate, polysorbates, sorbitan esters, stearyl alcohol, tyloxapol, tragacanth, xanthan gum, acacia, agar, alginic acid, sodium alginate, bentonite, carbomer, carboxymethyl cellulose sodium, cholesterol, gelatin, hydroxyethyl cellulose, hydroxypropyl cellulose, octoxynol, oleyl alcohol, polyvinyl alcohol, povidone, propylene glycol monostearate, sodium lauryl sulfate, and others known to those of ordinary skill in the art.

The formulation of the invention can also include water, organic solvent(s) and combinations thereof. In particular embodiments, the formulation includes alcohol, water, and saline. Specific embodiments of the invention include pyrogen-free, sterile water as liquid carrier. The water can comprise other components described herein. Water suitable for injection is suitable for use in the liquid formulation of the invention.

The formulation of the invention can also include biological salt(s), sodium chloride, potassium chloride, or other electrolyte(s).

The chemical stability of the liquid formulations of the invention, in terms of the formation of the above-mentioned dimer, can be enhanced by: adding an antioxidant, adjusting the pH of the liquid carrier, and/or eliminating or minimizing the presence of oxygen in the formulation. The chemical stability can also be enhanced by converting the liquid formulation to a solid formulation.

Generally, the least amount of propofol degradation (least amount of dimer formation) occurs in the presence of an antioxidant and with a nitrogen purge of the liquid formulations and the headspace of vials containing the liquid formulation during manufacture. The optimal pH may depend upon the nature of the antioxidant used as well as the physical properties of the propofol.

An antioxidant may be but need not be added to the formulation of the invention. Preferred antioxidants include EDTA (edetate), sodium metabisulfite and pentetate, for example. The EDTA is generally present in amounts which total less than about 0.1% by wt. based upon the total weight of the formulation, or about $3\times10^{-5}$ to about $9\times10^{-4}$ M, $3\times10^{-5}$ to $7.5\times10^{-4}$ M, $5\times10^{-5}$ to $5\times10^{-4}$ M, or $1.5\times10^{-4}$ to $3.0\times10^{-4}$ M or about 0.001% wt. by based upon the total weight of the formulation. The sodium metabisulfite is generally present in amounts from about 0.0075% to about 0.66% wt., and from about 0.0075% to about 0.1% wt. The pentetate is generally present in amounts which total less than about 0.3% by wt., or about 0.1% wt. to about 0.0005% wt. based upon the total weight of the formulation.

The liquid formulation can include a buffering agent, acidifying agent, alkalizing agent or combination thereof as a means of controlling the pH of the liquid. The pH of the liquid formulation will generally range from about 4.5–9.5. In one embodiment, the pH of the liquid formulation approximates the pH of blood or plasma. Exemplary buffering agents, acidifying agents and alkalizing agents are disclosed herein. In one embodiment, the buffering agent is a phosphate or citrate buffer present at a concentration of about 0.01 M of the liquid formulation, with a pH of 5.0 to 7.5.

Since propofol is subject to oxidative degradation resulting in the formation of a dimer, the liquid formulation will generally have its oxygen removed. For example, the headspace of the container with the liquid formulation is made oxygen free by purging the headspace with an inert gas, such as nitrogen or argon, or by bubbling the inert gas through the liquid formulation. For long-term storage, the liquid formulation is preferably stored in an oxygen-free or oxygen-reduced environment. The liquid formulation will generally contain less than about 5.0 ppm of oxygen. Removal of oxygen from the formulation, however, is not necessary to form a suitable stable formulation.

Propofol is also subject to light catalyzed degradation. Therefore, the liquid formulation is generally stored in a light-resistant or lightproof container. Suitable containers, such as vials, bottles, syringes or ampoules, can be made of amber-colored glass, light-blocking plastic, or paper, plastic, foil, metal or otherwise covered glass and/or plastic. The combined use of an antioxidant, light-resistant or lightproof container and an oxygen-free or oxygen-reduced environment provides the greatest protection against degradation of the propofol.

The light catalyzed degradation of propofol in the liquid and solid formulations of the invention was compared to the degradation in the marketed DIPRIVAN® formulation. Aliquots of the DIPRIVAN® formulation, an aqueous formulation containing 10 mg/mL propofol and 220 mg/mL CAPTISOL® cyclodextrin, and a solid formulation containing propofol and CAPTISOL® cyclodextrin, prepared by lyophilizing the aqueous propofol/CAPTISOL® cyclodextrin solution, were placed in clear glass vials in duplicate. One vial of each formulation was wrapped in aluminum foil to exclude all light, and the vials were exposed to 1.2 million lux-hours of fluorescent light. The samples were assayed by high performance liquid chromatography with ultraviolet detection for the presence of propofol and the dimer degradation product. Duplicate aliquots of the three formulations were also placed into quartz spectrophotometer cells. One cell containing each formulation was wrapped in aluminum foil to exclude light. The cells were exposed to 200 watt-hours/square meter of ultraviolet light and assayed as above. An external control sample for each formulation was stored at 2–8° C. in the absence of light for the duration of the study, and then analyzed. The results are given in the table below and indicate that the control samples showed no loss of propofol content over the course of the study. Both the solution and the solid CAPTISOL® cyclodextrin /propofol formulations demonstrated less degradation of the propofol than the DIPRIVAN® formulation. The table includes data regarding the percentage of propofol remaining in the samples after treatment with light. (*Values are relative to the foil wrapped controls)

| CONDITIONS | DIPRIVAN® emulsion | CAPTISOL® cyclodextrin/ propofol solution | CAPTISOL® cyclodextrin/ propofol solid |
|---|---|---|---|
| Control at 2–8° C. | 100 | 100 | 100 |
| Fluorescent Light Exposure* | 89.7 | 99.7 | 99.7 |
| Ultraviolet Light Exposure* | 97.1 | 99.3 | 97.2 |

The stability of propofol toward formation of the dimer 4,4'-dihydroxy-3,3',5,5'-tetraisopropyl-biphenyl was tested by exposure to ultraviolet light and fluorescent light with a control stored refrigerated in the dark. The tables below depict the effect that the preservatives disodium EDTA and sodium metabisulfite have on the dimerization of propofol. The amounts indicated in the columns refer to the concentration (mg/mL) of dimer present in solution after exposure to the specified conditions.

| | Refrigerated Storage (6 days, 2–8° C.) | UV Exposure (217 Wh/m$^2$) | Fluorescence Exposure (1200 klux hrs) |
|---|---|---|---|
| Formulations Containing 0.005% EDTA | | | |
| Diprivan, pH 7–8.5 | 0.000 | 0.010 | 0.011 |
| 0.1 M Captisol®, pH 7.3 | 0.000 | 0.000 | 0.000 |
| 0.2 M Captisol®, pH 7.5 | 0.000 | 0.000 | 0.000 |
| 0.1 M HP7-β-CD, pH 6.8 | 0.000 | 0.000 | 0.000 |
| 0.2 M HP4-β-CD, pH 7.4 | 0.000 | 0.000 | 0.000 |
| Formulations Containing | | | |

-continued

|  | Refrigerated Storage (6 days, 2–8° C.) | UV Exposure (217 Wh/m$^2$) | Fluorescence Exposure (1200 klux hrs) |
|---|---|---|---|
| 0.025% Sodium Metabisulfate |  |  |  |
| Baxter Emulsion, pH 4.5–6.4 | 0.013 | 0.033 | 0.055 |
| 0.1 M Captisol ®, pH 5.3 | 0.000 | 0.008 | 0.014 |
| 0.2 M Captisol ®, pH 5.6 | 0.000 | 0.015 | 0.007 |
| 0.1 M HP7-β-CD, pH 5.5 | 0.001 | 0.001 | 0.003 |
| 0.1 M HP4-β-CD, pH 6.0 | 0.001 | 0.001 | 0.004 |

Accordingly, the SAE-CD containing formulation of the invention stabilizes the propofol toward dimerization as compared to either emulsion-type formulation.

The SAE-CD formulations demonstrate reduced support for microbial growth as compared to the lipid emulsion formulations. In side-by-side comparisons, three different SAE-CD containing solutions were compared to the lipid emulsion containing DIPRIVAN® and Baxter, Propofol Injectable Emulsion, formulations in terms of their ability to sustain microbial growth. Each of the SAE-CD containing solutions contained propofol (1% wt.) and SBE7-β-CD (22% w/v). In addition, one of the three solutions contained disodium EDTA (0.005% w/v) at pH 8.2 to mimic the DIPRIVAN® formulation, and another of the three solutions contained sodium metabisulfite (0.025% w/v) at pH 5.5 to mimic the Baxter formulation. The third solution contained no added preservative per se. The data indicate that the SAE-CD does not sustain microbial growth. Moreover, the SAE-CD containing formulations actually had a lower microbial count after 24 and 48 hours than they did at the beginning of the study. Accordingly, the present formulation provides a substantially preserved parenteral formulation comprising an SAE-CD and a sedative hypnotic agent. Unlike the emulsion formulation, the present formulation or composition does not require an added preservative, such as detailed below; although, a preservative can be included. As such, the presently claimed formulations unexpectedly possess microbial growth retarding or preservative properties as compared to the lipid emulsion containing formulations.

Unlike the prior art, specific embodiments of the present formulation are substantially lipid-free, or they can contain no lipid.

The liquid formulation of the invention can be provided in an ampoule, syringe, bottle, vial or other such container typically used for parenteral formulations.

Other therapeutic agents such as local anesthetics can be included in the formulation of the invention. When present, these other therapeutic agents may or may not bind or complex with the SAE-CD. It is only necessary that the SAE-CD be present in the formulation in an amount sufficient to solubilize the sedative hypnotic in the presence of the added therapeutic agent. Representative local anesthetics include benzocaine, procaine, lidocaine, piperocaine, tetracaine, lignocaine, prilocaine, bupivacaine, proxymetacaine, ropivacaine, and dibucaine.

The liquid formulation of the invention can be prepared by numerous different methods. According to one method, a first aqueous solution comprising SAE-CD is prepared. Then, a second solution comprising a sedative hypnotic is prepared. Finally, the first and second solutions are mixed to form the liquid formulation. The first and second solutions can independently comprise other excipients and agents described herein. Additionally, the second solution can be water and/or organic solvent-based.

Another method of preparation is similar to the above-described method except that the sedative hypnotic is added directly to the first solution without formation of the second solution.

A third method of preparing the liquid formulation is similar to the above-described first method except that the SAE-CD is added directly to an aqueous second solution containing the sedative hypnotic without formation of the first solution.

A fourth method of preparing the liquid formulation comprises the steps of adding an aqueous solution comprising a sedative hypnotic to a powdered or particulate SAE-CD and mixing the solution until the SAE-CD has dissolved.

The liquid formulation of the invention can be provided in a kit. The kit will comprise a first pharmaceutical composition comprising an SAE-CD and a second pharmaceutical composition comprising a sedative hypnotic agent. The first and second formulations can be mixed and formulated as a liquid dosage form prior to administration to a subject. Either one or both of the first and second pharmaceutical compositions can comprise additional pharmaceutical excipients. The kit is available in various forms.

In a first kit, the first and second pharmaceutical compositions are provided in separate containers or in separate chambers of a container having two or more chambers. The first and second pharmaceutical compositions may be independently provided in solid or liquid form. For example, the SAE-CD can be provided in a reconstitutable powder form and the sedative hypnotic agent can be provided in solid (below 19° C.) form. According to one embodiment the kit would further comprise a pharmaceutically acceptable liquid carrier used to suspend and dissolve the first and/or second pharmaceutical compositions. Alternatively, a liquid carrier is independently included with the first and/or second pharmaceutical composition. The liquid carrier, however, can also be provided in a container or chamber separate from the first and second pharmaceutical compositions. As above, the first pharmaceutical composition, the second pharmaceutical composition and the liquid carrier can independently comprise a preservative, an antioxidant, a buffering agent, an acidifying agent, saline, an electrolyte, another therapeutic agent, an alkalizing agent, an antimicrobial agent, an antifungal agent, solubility enhancing agent or a combination thereof.

The liquid formulation of the invention can be provided as a dosage form including a prefilled vial, prefilled bottle, prefilled syringe, prefilled ampoule or plural ones thereof. Generally, a prefilled container will contain at least a unit dosage form of the sedative hypnotic agent.

The term "unit dosage form" is used herein to mean a single or multiple dose form containing a quantity of the active ingredient and the diluent or carrier, said quantity being such that one or more predetermined units are normally required for a single therapeutic administration. In the case of multiple dose forms, such as liquid-filled ampoules, said predetermined unit will be one fraction such as a half or quarter of the multiple dose form. It will be understood that the specific dose level for any patient will depend upon a variety of factors including the indication being treated, the therapeutic agent employed, the activity of the therapeutic agent, severity of the indication, patient health, age, sex, weight, diet, and pharmacological response, the specific dosage form employed and other such factors.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "patient" is taken to mean warm blooded animals such as mammals, for example, cats, dogs, mice, guinea pigs, horses, bovine cows, sheep and humans.

The liquid formulation of the invention will comprise an effective amount of propofol. By the term "effective amount", it is understood that a therapeutically effective amount is contemplated. A therapeutically effective amount is the amount or quantity of propofol that is sufficient to elicit the required or desired therapeutic response, or in other =words, the amount that is sufficient to elicit an appreciable biological response when administered to a subject.

As noted above, emulsion-type formulations generally cannot be sterile filtered as doing so would either clog the filter or disrupt the emulsion. The present formulation containing SAE-CD and a sedative hypnotic agent can be sterile filtered through filters having pores sizes of 0.1 microns or larger, or pore sizes of about 0.1 microns, 0.2 microns, 0.22 microns, 0.3 microns, 0.45 microns or larger. Accordingly, a method of preparing a sterile SAE-CD/sedative hypnotic formulation can comprise the step of sterile filtering the formulation through a filtration medium having a pore size of 0.1 microns or larger.

As with other sedative hypnotic-containing formulations, the present formulation is used to induce hypnosis, induce sedation and/or maintain sedation in a subject. Hypnosis and sedation are induced by administering to a subject a sufficient amount of the liquid formulation of the invention, by injection or infusion, over a sufficient period of time to induce hypnosis and/or sedation in the subject. Sedation is maintained by administering a sufficient amount of the liquid formulation of the invention, by periodic injection or continuous infusion. In general, induction of hypnosis or sedation can be performed by rapid or slow administration of the sedative hypnotic depending upon the needs of a particular subject. Maintenance of sedation is typically conducted by administering a lower dose of sedative hypnotic to an already sedated subject. A subject may be previously sedated with another drug and then administered the sedative hypnotic according to the invention. Likewise, sedation or hypnosis can be induced in a subject with another drug and subsequently maintained by administration of a sedative hypnotic according to the invention. Other injectable agents used alone or in combination with the sedative hypnotic of the invention include the benzodiazepines such as midazolam, and flunitrazepam; narcotics such as morphine, buprenorphine, fentanyl, alfentanyl, sufentanyl, and remifentanyl; barbiturates such as thiopentone and methohexital; and other agents such as etomidate, ketamine, thiopentone, and alphaxalone/alphadolone.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

An exemplary formulation according to the invention was made according to the following general procedure. CAPTISOL® cyclodextrin was dissolved in water to form a solution containing about 220 mg/mL of CAPTISOL® cyclodextrin. Propofol was added to the SAE-CD containing solution until a concentration of about 10 mg/niL propofol was reached. A formulation currently being evaluated in animal and clinical pain-on-injection studies and comprising the following components in the amounts indicated was prepared as indicated above.

| Ingredient | Amount | Value |
|---|---|---|
| Propofol | 10 mg/mL | 0.056 Molar (mw = 178.28) |
| CAPTISOL ® cyclodextrin | 220 mg/mL | 0.102 Molar (mw = 2163) |
| Sterile Water for Injection | to volume | |

The pH of the solution was not adjusted and no antioxidants or preservatives were included.

EXAMPLE 2

The procedure of Example 1 was followed to prepare a general liquid formulation comprising propofol and an SAE-CD, which included the following ingredients in the approximate amounts indicated.

| Ingredient | Amount |
|---|---|
| Propofol | 10 mg/mL ± about 10% wt. |
| CAPTISOL ® cyclodextrin | Sufficient to form a CAPTISOL ® cyclodextrin/propofol molar ratio of about 1.1:1 to 2:1 and to yield a CAPTISOL ® cyclodextrin concentration of about 145–270 mg/mL, wherein CAPTISOL ® cyclodextrin has a molecular weight of about 2163. (It is noted that the exact weight of CAPTISOL ® cyclodextrin used will vary depending upon the specific molecular weight of the batch of CAPTISOL ® cyclodextrin being used.) |
| Water | q.s. |

EXAMPLE 3

| Ingredient | Amount | Value |
|---|---|---|
| Propofol | 10 mg/mL | 0.056 Molar (mw = 178.28) |
| CAPTISOL ® cyclodextrin | 216 mg/mL | 0.100 Molar (mw = 2163) |
| EDTA | 0.1 mg/mL | 0.01% w/v |
| Water | to volume | |

CAPTISOL® cyclodextrin was dissolved in water to form a solution containing about 0.1 Molar (approximately 216 mg/mL) of CAPTISOL® cyclodextrin. Disodium ethylenediaminetetraacetate was added to the CAPTISOL® cyclodextrin solution at 0.01% w/v and dissolved. Propofol was then added to the SAE-CD containing solution with stirring until a concentration of about 10 mg/mL propofol was reached. The pH was then adjusted to 7–8.5 with sodium hydroxide. The solution was purged with nitrogen gas then filtered through a 0.22 micron pore size filter into a sterilized glass vial. The headspace of the vial was purged with sterile filtered nitrogen gas and the vial was sealed.

EXAMPLE 4

| Ingredient | Amount | Value |
|---|---|---|
| Propofol | 20 mg/mL | 0.112 Molar (mw = 178.28) |
| CAPTISOL ® cyclodextrin | 432 mg/mL | 0.200 Molar (mw = 2163) |
| Water | to volume | |

CAPTISOL® cyclodextrin was dissolved in water to form a solution containing about 0.2 Molar (approximately 432 mg/mL) of CAPTISOL® cyclodextrin. Propofol was then added to the SAE-CD containing solution with stirring until a concentration of about 20 mg/mL propofol was reached. The solution was lyophilized to generate a solid formulation. Prior to use as a solution, sufficient sterile water for injection is added to the solid formulation to generate a final solution containing propofol 10 mg/mL.

EXAMPLE 5

A formulation of the invention containing 10 mg/mL propofol and 220 mg/mL CAPTISOL® cyclodextrin was mixed with a 2% aqueous lidocaine solution in volume ratios of 5:1 and 9:1 (propofol formulation:lidocaine formulation). Both formulations provided clear solutions. Accordingly, the formulation of the invention can include a second therapeutic agent, such as a local anesthetic, in combination with the propofol and SAE-CD without effecting precipitation of the propofol, in other words, while still maintaining a clear solution. In a combination parenteral formulation, it is only necessary that the SAE-CD be present in an amount sufficient to render the solution clear even in the presence of both therapeutic agents. For nonparenteral, e.g., oral, formulations, the combination formulation need not retain its clarity and can be formulated as a suspension.

EXAMPLE 6

The growth retarding capability of three 1% propofol injectable solutions complexed with a sulfoalkyl ether cyclodextrin were evaluated and compared with two marketed products: DIPRIVAN® Injectable Emulsion 1% and Propofol Injectable Emulsion 1%. The products were evaluated in duplicate employing a liquid to liquid matrix against seven test organisms, at three exposure intervals, and at two exposure temperatures, then quantitated using membrane filtration. Approximately 50–200 colony formation units (CFU) per mL of five standard organisms recommended by United States Pharmacopoeia (USP) for preservative efficacy tests were inoculated in each formulation. These five organisms are identified as *Staphylococcus aureus* (ATCC 6538), *Pseudomonas aeruginosa* (ATCC 9027), *Escherichia coil* (ATCC 8739), *Aspergillus niger* (ATCC 16404) and *Candida albicans* (ATCC 10231). In addition to these organisms, *Staphylococcus epidermis* (ATCC 12228) and *Staphylococcus aureus* methicillin resistant *staphylococcus aureus* (MRSA) (ATCC 700698) were also tested.

The antimicrobial activity of three products containing Captisol® cyclodextrin and propofol (a first product containing no preservative per se, a second containing the preservative disodium EDTA 0.005% w/v at pH 8.2, and a third containing sodium metabisulfite 0.025% w/v at pH 5.5), were evaluated to determine the ability to support microbial growth after specific exposure temperatures and time intervals. Two marketed products, Diprivan Injectable Emulsion 1% and Propofol Injectable Emulsion 1%, were tested in parallel for comparison. After the samples were incubated at 20–25° C. or 30–35° C., they were inoculated with the test organisms to yield approximately 50–200 colony forming units (CFU)/mL. The viable count of the test organism was determined immediately following inoculation, and then after 24 and 48 hours of exposure. An aliquot of the test sample-cell suspension was suspended with peptone Tween® solution, filtered using a 0.45 μm filter, washed with a peptone Tween® solution and the membrane was transferred to a neutralized agar plate. The plates were incubated at 35–39° C. for 24–72 hours for bacteria, et 20–25° C. for 48–72 hours for the yeast, and at 20–25° C. for 4–10 days for the mold. This study was verified using a neutralization procedure to ensure that the recovery medium is capable of neutralizing any residual preservative when the test aliquots were drawn and filtered.

The following Tables 1–14 compare the antimicrobial effectiveness of Captisol® cyclodextrin solutions of propofol with that of DIPRIVAN® Injectable Emulsion 1% and Propofol Injectable Emulsion 1% solutions. These results indicate that formulations of propofol containing Captisol® cyclodextrin possess microbial growth retarding or preservative properties and are capable of decreasing the content of viable microorganisms for at least 48 hours after adventitious, extrinsic contamination with bacteria, yeast and mold. The emulsion formulations supported the growth of each of the bacteria, allowing increased numbers of viable microorganisms to be present after the incubation period.

TABLE 1

Comparison of microbial growth retarding activity of various formulations against *S. aureus* (ATCC 6538) incubation at 20–25° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 2.59 ± 0.03 | ND | ND | 2.59 | 2.59 |
| Captisol ® #2 | 2.63 ± 0.02 | ND | ND | 2.63 | 2.63 |
| Captisol ® #3 | 2.65 ± 0.02 | ND | ND | 2.65 | 2.65 |
| Diprivan Injectable Emulsion 1% | 2.69 ± 0.04 | 4.31 ± 0.01 | 6.78 ± 0.11 | NA | NA |
| Propofol Injectable Emulsion 1% | 2.68 ± 0.06 | 4.35 ± 0.33 | 5.60 ± 0.08 | NA | NA |

NA: Not applicable, ND: No viable organisms detected in 1 mL aliquot, SD: standard deviation, Captisol ® #1: 1% Propofol, 22% w/v Captisol, Captisol ® #2: 1% Propofol, 22% w/v Captisol, 0.005% w/v disodium EDTA, Captisol ® #3: 1% Propofol, 22% w/v Captisol, 0.025% w/v sodium metabisulfate.

TABLE 2

Comparison of microbial growth retarding activity of various formulations against *S. aureus* (ATCC 6538) incubation at 30–35° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 2.63 ± 0.01 | ND | ND | 2.63 | 2.63 |
| Captisol ® #2 | 2.65 ± 0.03 | ND | ND | 2.65 | 2.65 |
| Captisol ® #3 | 2.65 ± 0.01 | ND | ND | 2.65 | 2.65 |
| Diprivan Injectable Emulsion 1% | 2.54 ± 0.01 | 5.23 ± 0.44 | 6.56 ± 0.09 | NA | NA |
| Propofol Injectable Emulsion 1% | 2.63 ± 0.06 | 5.79 ± 0.30 | 6.89 ± 0.01 | NA | NA |

TABLE 3

Comparison of microbial growth retarding activity of various formulations against *E. coli* (ATCC 8739) incubation at 20–25° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 2.47 ± 0.04 | 0.96 ± 1.35 | ND | 1.51 | 2.47 |
| Captisol ® #2 | 2.58 ± 0.04 | 0.30 ± 0.42 | ND | 2.28 | 2.58 |
| Captisol ® #3 | 2.56 ± 0.07 | 0.15 ± 0.21 | 0.52 ± 0.74 | 2.41 | 2.04 |
| Diprivan Injectable Emulsion 1% | 2.53 ± 0.08 | 5.96 ± 0.02 | 7.98 ± 0.03 | NA | NA |
| Propofol Injectable Emulsion 1% | 2.58 ± 0.01 | 6.40 ± 0.04 | 7.81 ± 0.33 | NA | NA |

TABLE 4

Comparison of microbial growth retarding activity of various formulations against *E. coli* (ATCC 8739) incubation at 30–35° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 2.50 ± 0.01 | ND | ND | 2.50 | 2.50 |
| Captisol ® #2 | 2.46 ± 0.04 | ND | ND | 2.46 | 2.46 |
| Captisol ® #3 | 2.57 ± 0.05 | ND | ND | 2.57 | 2.57 |

TABLE 4-continued

Comparison of microbial growth retarding activity of various formulations against *E. coli* (ATCC 8739) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Diprivan Injectable Emulsion 1% | 2.67 ± 0.01 | 6.90 ± 0.84 | 7.92 ± 0.08 | NA | NA |
| Propofol Injectable Emulsion 1% | 2.71 ± 0.04 | 7.76 ± 0.28 | 7.68 ± 0.67 | NA | NA |

TABLE 5

Comparison of microbial growth retarding activity of various formulations against *C. albicans* (ATCC 10231) incubation at 20–25° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.45 ± 0.01 | ND | ND | 2.45 | 2.45 |
| Captisol ® #2 | 2.41 ± 0.03 | ND | ND | 2.41 | 2.41 |
| Captisol ® #3 | 2.44 ± 0.08 | ND | ND | 2.44 | 2.44 |
| Diprivan Injectable Emulsion 1% | 2.39 ± 0.04 | 2.46 ± 0.07 | 2.50 ± 0.18 | NA | NA |
| Propofol Injectable Emulsion 1% | 2.43 ± 0.01 | 3.14 ± 0.86 | 3.55 ± 1.27 | NA | NA |

TABLE 6

Comparison of microbial growth retarding activity of various formulations against *C. albicans* (ATCC 10231) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.45 ± 0.06 | ND | ND | 2.45 | 2.45 |
| Captisol ® #2 | 2.41 ± 0.04 | ND | ND | 2.41 | 2.41 |
| Captisol ® #3 | 2.43 ± 0.00 | ND | ND | 2.43 | 2.43 |
| Diprivan Injectable Emulsion 1% | 2.50 ± 0.05 | 2.58 ± 0.23 | 2.81 ± 0.57 | NA | NA |
| Propofol Injectable Emulsion 1% | 2.50 ± 0.03 | 3.17 ± 0.76 | 4.69 ± 0.05 | NA | NA |

TABLE 7

Comparison of microbial growth retarding activity of various formulations against *S. epidermis* (ATCC 12228) incubation at 20–25° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.37 ± 0.04 | ND | ND | 2.37 | 2.37 |
| Captisol ® #2 | 2.38 ± 0.06 | ND | ND | 2.38 | 2.38 |
| Captisol ® #3 | 2.38 ± 0.02 | ND | ND | 2.38 | 2.38 |
| Diprivan Injectable Emulsion 1% | 2.43 ± 0.02 | 2.47 ± 0.08 | 2.43 ± 0.14 | NA | NA |
| Propofol Injectable Emulsion 1% | 2.40 ± 0.00 | 2.59 ± 0.11 | 2.68 ± 0.11 | NA | NA |

TABLE 8

Comparison of microbial growth retarding activity of various formulations against *S. epidermis* (ATCC 12228) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.37 ± 0.02 | ND | ND | 2.37 | 2.37 |
| Captisol ® #2 | 2.35 ± 0.06 | ND | ND | 2.35 | 2.35 |

TABLE 8-continued

Comparison of microbial growth retarding activity of various formulations against *S. epidermis* (ATCC 12228) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #3 | 2.39 ± 0.04 | ND | ND | 2.39 | 2.39 |
| Diprivan Injectable Emulsion 1% | 2.40 ± 0.01 | 2.63 ± 0.00 | 2.75 ± 0.04 | NA | NA |
| Propofol Injectable Emulsion 1% | 2.34 ± 0.05 | 5.44 ± 0.33 | 7.52 ± 0.34 | NA | NA |

TABLE 9

Comparison of microbial growth retarding activity of various formulations against *S. aureus* (MSRA) (ATCC 700698) incubation at 20–25° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.36 ± 0.04 | ND | ND | 2.36 | 2.36 |
| Captisol ® #2 | 2.38 ± 0.07 | ND | ND | 2.38 | 2.38 |
| Captisol ® #3 | 2.32 ± 0.02 | ND | ND | 2.32 | 2.32 |
| Diprivan Injectable Emulsion 1% | 2.57 ± 0.08 | 3.52 ± 0.06 | 5.73 ± 1.12 | NA | NA |
| Propofol Injectable Emulsion 1% | 2.43 ± 0.03 | 3.48 ± 0.72 | 5.24 ± 0.28 | NA | NA |

TABLE 10

Comparison of microbial growth retarding activity of various formulations against *S. aureus* (MSRA) (ATCC 700698) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.40 ± 0.02 | ND | ND | 2.40 | 2.40 |
| Captisol ® #2 | 2.33 ± 0.01 | ND | ND | 2.33 | 2.33 |
| Captisol ® #3 | 2.39 ± 0.01 | ND | ND | 2.39 | 2.39 |
| Diprivan Injectable Emulsion 1% | 2.47 ± 0.06 | 4.23 ± 0.21 | 6.06 ± 0.84 | NA | NA |
| Propofol Injectable Emulsion 1% | 2.41 ± 0.00 | 5.68 ± 0.28 | 6.31 ± 0.22 | NA | NA |

TABLE 11

Comparison of microbial growth retarding activity of various formulations against *P. aeruginosa* (ATCC 9027) incubation at 20–25° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.21 ± 0.03 | 0.89 ± 1.25 | 0.93 ± 1.32 | 1.32 | 1.28 |
| Captisol ® #2 | 2.10 ± 0.00 | 0.88 ± 1.24 | ND | 1.22 | 2.10 |
| Captisol ® #3 | 2.21 ± 0.03 | ND | ND | 2.21 | 2.21 |
| Diprivan Injectable Emulsion 1% | 2.42 ± 0.01 | 5.14 ± 0.08 | 7.97 ± 0.11 | NA | NA |
| Propofol Injectable Emulsion 1% | 2.32 ± 0.06 | 5.45 ± 0.02 | 7.86 ± 0.07 | NA | NA |

TABLE 12

Comparison of microbial growth retarding activity of various formulations against *P. aeruginosa* (ATCC 9027) incubation at 30–35° C.

| Formulation | Viable count of Survivors log₁₀ CFU/mL ± SD | | | Decrease in survivors log₁₀ CFU/mL | |
|---|---|---|---|---|---|
| | 0 h | 24 h | 48 h | 24 h | 48 h |
| Captisol ® #1 | 2.29 ± 0.02 | ND | ND | 2.29 | 2.29 |
| Captisol ® #2 | 2.07 ± 0.03 | ND | ND | 2.07 | 2.07 |

TABLE 12-continued

Comparison of microbial growth retarding activity of various formulations against *P. aeruginosa* (ATCC 9027) incubation at 30–35° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #3 | 2.09 ± 0.03 | 1.80 ± 0.30 | 1.97 ± 0.51 | 0.29 | 0.12 |
| Diprivan Injectable Emulsion 1% | 2.32 ± 0.06 | 5.08 ± 0.00 | 8.02 ± 0.08 | NA | NA |
| Propofol Injectable Emulsion 1% | 2.21 ± 0.03 | 8.27 ± 0.01 | 8.38 ± 0.05 | NA | NA |

TABLE 13

Comparison of microbial growth retarding activity of various formulations against *A. niger* (ATCC 16404) incubation at 20–25° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 0.95 ± 0.00 | 0.15 ± 0.21 | ND | 0.8 | 0.95 |
| Captisol ® #2 | 0.93 ± 0.04 | 0.24 ± 0.34 | 0.24 ± 0.34 | 0.69 | 0.69 |
| Captisol ® #3 | 0.93 ± 0.11 | 0.30 ± 0.42 | 0.54 ± 0.34 | 0.63 | 0.39 |
| Diprivan Injectable Emulsion 1% | 1.08 ± 0.05 | 0.72 ± 0.33 | 0.54 ± 0.08 | 0.36 | 0.54 |
| Propofol Injectable Emulsion 1% | 0.59 ± 0.39 | ND | ND | 0.59 | 0.59 |

TABLE 14

Comparison of microbial growth retarding activity of various formulations against *A. niger* (ATCC 16404) incubation at 30–35° C.

| Formulation | Viable count of Survivors $\log_{10}$ CFU/mL ± SD | | | Decrease in survivors $\log_{10}$ CFU/mL | |
|---|---|---|---|---|---|
| | 0 h | 24 h | 48 h | 24 h | 48 h |
| Captisol ® #1 | 0.63 ± 0.46 | 0.59 ± 0.16 | 0.39 ± 0.13 | 0.04 | 0.24 |
| Captisol ® #2 | 0.84 ± 0.08 | 0.63 ± 0.21 | 0.43 ± 0.60 | 0.21 | 0.41 |
| Captisol ® #3 | 0.80 ± 0.14 | 0.72 ± 0.33 | 0.24 ± 0.34 | 0.08 | 0.56 |
| Diprivan Injectable Emulsion 1% | 0.73 ± 0.18 | 0.91 ± 0.18 | 0.30 ± 0.42 | NA | 0.43 |
| Propofol Injectable Emulsion 1% | 0.78 ± 0.11 | ND | ND | 0.78 | 0.78 |

The clarity of the liquid formulations described herein can be determined visually by comparison to standard solutions of known clarity. The clarity can also be determined by transmittance spectrophotometry at a wavelength of 800 nm. Using either method, the solutions prepared according to the invention were determined to be at least visually clear.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A clear pharmaceutical aqueous liquid formulation comprising:

propofol;

a sulfoalkyl ether cyclodextrin (SAE-CD); and an aqueous liquid carrier, wherein the molar ratio of SAE-CD to propofol is in the range of about 1:1 to 5:1; and wherein the propofol is present in an amount of about 1 to 55 mg/mL; and the SAE-CD is present in an amount of about 0.005 M to 0.37 M.

2. The formulation of claim 1, wherein the SAE-CD is a compound of the Formula 1 or a combination thereof wherein:

Formula 1

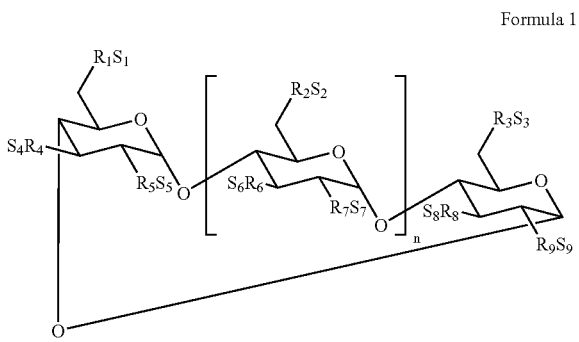

n is 4, 5 or 6;

$R_1$, $R_2$, $R_3$, $R_4$, $R_5$, $R_6$, $R_7$, $R_8$, and $R_9$, are each, independently, —O— or a —O—(C2–C6 alkylene)-$SO_3^-$ group, wherein at least one of $R_1$ and 1(2 is independently a —O—(C2–C6 alkylene)-$SO_3^-$ group; and $S_1$, $S_2$, $S_3$, $S_4$, $S_5$, $S_6$, $S_7$, $S_8$ and $S_9$ are each a pharmaceutically acceptable cation.

3. The formulation of claim 2, wherein the molar ratio of SAE-CD to propofol is in the range of about 1.1:1 to 2.0:1.

4. The formulation of claim 3, wherein the SAE-CD is SBE-7-β-CD or SBE-4-β-CD.

5. The formulation of claim 3, wherein the propofol is present in an amount of about 0.1 to 5.0% by wt. based upon the total weight of the liquid formulation.

6. The formulation of claim 3, wherein the propofol is present in an amount of about 0.1 to 2.0% by wt.

7. The formulation of claim 3, wherein the SAE-CD is present in an amount of about 3 to 80% w/v.

8. The formulation of claim 1, 3, 2 or 4 further comprising a preservative, antioxidant, buffering agent, acidifying agent, alkalizing agent, antibacterial agent, antifungal agent, solubility enhancing agent, complexation enhancing agent, organic solvent, electrolyte, salt, stabilizer, tonicity modifier, antifoaming agent or a combination thereof.

9. The formulation of claim 8, wherein the antioxidant is present and is EDTA present in an amount of about $3\times10^{-5}$ to about $9\times10^{-4}$ M, pentetate present in an amount of about 0.0005% to about 0.3% by wt. or a metabisulfite salt present in an amount from about 0.0075% to about 0.66% by wt.

10. The formulation of claim 8, wherein the formulation comprises less than about 5 ppm of oxygen gas.

11. The formulation of claim 1, 3, 2 or 4 further comprising one or more local anesthetic agents, wherein the SAE-CD is present in an amount sufficient to solubilize the propofol in the presence of the one or more local anesthetic agents.

12. The formulation of claim 11, wherein the local anesthetic agent is selected from the group consisting of procaine, lidocaine, piperocaine, tetracaine, lignocaine, prilocaine, bupivacaine, proxymetacaine, ropivacaine, dibucaine and a combination thereof.

13. The formulation of claim 2, wherein the molar ratio of SAE-CD to propofol is in the range of about 2.0:1 to 4.6:1.

14. The formulation of claim 13, wherein the propofol is present in an amount of about 0.1 to 5.0% by wt. based upon the total weight of the liquid formulation.

15. The formulation of claim 13, wherein the propofol is present in an amount of about 0.1 to 2.0% by wt.

16. The formulation of claim 13, wherein the SAE-CD is present in an amount of about 3 to 80% w/v.

17. The formulation of claim 13, 14, 15 or 16 further comprising a preservative, antioxidant, buffering agent, acidifying agent, alkalizing agent, antibacterial agent, antifungal agent, solubility enhancing agent, another therapeutic agent, complexation enhancing agent, organic solvent, electrolyte, salt, stabilizer, tonicity modifier, antifoaming agent or a combination thereof.

18. The formulation of claim 17, wherein the antioxidant is present and is EDTA present in an amount of about $3\times10^{-5}$ to about $9\times10^{-4}$ M, pentetate present in an amount of about 0.0005% to about 0.3% by wt. or a metabisulfite salt present in an amount from about 0.0075% to about 0.66% by wt.

19. The formulation of claim 17, wherein the other therapeutic agent is present and is a local anesthetic and the SAE-CD is present in amount sufficient to solubilize the propofol in the presence of the local anesthetic.

20. The formulation of claim 19, wherein the local anesthetic agent is selected from the group consisting of procaine, lidocaine, piperocaine, tetracaine, lignocaine, prilocaine, bupivacaine, proxymetacaine, ropivacaine, dibucaine and a combination thereof.

21. The formulation of claim 2, wherein the liquid formulation has been sterile filtered through a filtration medium having a pore size of about 0.45 microns or smaller.

22. A pharmaceutical kit consisting essentially of:
 a first pharmaceutical composition comprising an SAE-CD of the Formula 1; and
 a second pharmaceutical composition comprising propofol;
 wherein the molar ratio of SAE-CD to propofol is in the range of about 1:1 to 5:1; and
 at least the first and second pharmaceutical compositions can be mixed with an aqueous liquid carrier to form a clear liquid dosage form prior to administration to a subject comprising propofol present in an amount of about 1 to 55 mg/mL and SAE-CD present in an amount of about 0.005 M to 0.37 M.

23. The pharmaceutical kit of claim 22, wherein the first and second formulations independently comprise one or more pharmaceutical excipients selected from the group consisting of a preservative, an antioxidant, a buffering agent, an acidifying agent, saline, an electrolyte, another therapeutic agent, an alkalizing agent, an antimicrobial agent, an antifungal agent, a solubility enhancing agent, an emulsifying agent, oil, complexation enhancing agent or a combination thereof.

24. The pharmaceutical kit of claim 23, wherein the other therapeutic agent is present and is a local anesthetic.

25. The pharmaceutical kit of claim 22, wherein the first and second pharmaceutical compositions are provided in separate containers or in separate chambers of a container having two or more chambers.

26. The pharmaceutical kit of claim 22, wherein the kit further comprises a pharmaceutically acceptable liquid carrier used to form the liquid formulation.

27. The pharmaceutical kit of claim 26, wherein the liquid carrier is independently included with the first and/or second pharmaceutical composition.

28. The pharmaceutical kit of claim 26, wherein the liquid carrier is provided in a container or chamber separate from the first and second pharmaceutical compositions.

29. The pharmaceutical kit of claim 26, wherein the first pharmaceutical composition, the second pharmaceutical composition, the liquid carrier or a combination thereof further comprises a preservative, an antioxidant, a buffering agent, an acidifying agent, saline, an electrolyte, another therapeutic agent, an alkalizing agent, an antimicrobial agent, an antifungal agent, a solubility enhancing agent, an emulsifying agent, oil, complexation enhancing agent or a combination thereof.

30. The pharmaceutical kit of claim 29, wherein the other therapeutic agent is present and is a local anesthetic.

31. The pharmaceutical kit of claim 22, wherein the kit is provided chilled.

32. A method of administering propofol to a subject comprising the step of:
   administering to a subject by injection or intravenous infusion a clear aqueous liquid formulation comprising a sulfoalkyl ether cyclodextrin of the Formula 1 and propofol, wherein the molar ratio of SAE-CD to propofol is in the range of about 1:1 to 5:1, and propofol is present in an amount of about 1 to 20 mg/mL;
   and the SAE-CD is present in an amount of about 0.005 M to 0.37 M.

33. The method of claim 32, wherein the amount of propofol administered is sufficient to induce hypnosis or sedation in the subject.

34. The method of claim 32, wherein the amount of propofol administered is sufficient to maintain sedation in a subject in which sedation has already been induced.

35. The method of claim 32–33 or 34, wherein the liquid formulation provides an electroencephalographic response similar to that of an emulsion-type formulation comprising water, egg lecithin, oil, glycerol, preservative and a comparable amount of propofol.

36. The method of claim 32–33 or 34, wherein the liquid formulation provides a hemodynamic response similar to that of an emulsion-type formulation comprising water, egg lecithin, oil, glycerol, preservative and a comparable amount of propofol.

37. A method of administering propofol to a subject comprising the step of:
   administering to a subject by injection, intravenous infusion, or orally a liquid formulation according to claim 1, 3, 2, 4, 5–6 or 7.

38. A method of administering propofol to a subject comprising the step of:
   administering to a subject by injection, intravenous infusion, or orally a liquid formulation according to claim 8.

39. A method of administering propofol to a subject comprising the step of:
   administering to a subject by injection, intravenous infusion, or orally a liquid formulation according to claim 9.

40. A method of administering propofol to a subject comprising the step of:
   administering to a subject by injection, intravenous infusion, or orally a liquid formulation according to claim 11.

41. A method of administering propofol to a subject comprising the step of:
   administering to a subject by injection, intravenous infusion, or orally a liquid formulation according to claim 13, 14, or 16.

42. A method of administering propofol to a subject comprising the step of:
   administering to a subject by injection, intravenous infusion, or orally a liquid formulation according to claim 17.

43. A method of administering propofol to a subject comprising the step of:
   administering to a subject by injection, intravenous infusion, or orally a liquid formulation according to claim 19.

44. A reconstitutable solid pharmaceutical composition comprising:
   propofol and a sulfoalkyl ether cyclodextrin of the Formula 1, wherein the molar ratio of SAE-CD to propofol is in the range of about 1.1:1 to about 2.0:1; and wherein a clear liquid formulation is formed when the reconstitutable solid is mixed with an aqueous liquid carrier such that the propofol is present in an amount of about 1 to 55 mg/mL and SAE-CD is present in an amount of about 0.005 M to 0.37 M.

45. The composition of claim 44, wherein the composition comprises an admixture of a solid SAB-CD, propofol and optionally at least one solid pharmaceutical excipient, such that a major portion of the propofol is not complexed with the SAE-CD prior to reconstitution.

46. The composition of claim 44, wherein the composition comprises a solid mixture of an SAE-CD and propofol, wherein a major portion of the propofol is complexed with the SAE-CD prior to reconstitution.

47. The composition of claim 44, 45 or 46 further comprising a preservative, an antioxidant, a buffering agent, an acidifying agent, saline, an electrolyte, another therapeutic agent, an alkalizing agent, an antimicrobial agent, an antifungal agent, solubility enhancing agent, emulsifying agent, complexation enhancing agent, antifoaming agent, oil, or a combination thereof.

48. The composition of claim 47, wherein the other therapeutic agent is present and is a local anesthetic agent.

49. The composition of claim 48, wherein the local anesthetic agent is selected from the group consisting of procaine, lidocaine, piperocaine, tetracaine, lignocaine, prilocaine, bupivacaine, proxymetacaine, ropivacaine, and dibucaine.

50. A pharmaceutical kit comprising a first container or chamber containing a liquid vehicle and a second container or chamber containing a composition according to claim 44, 45 or 46.

51. The pharmaceutical kit of claim 50, wherein the pharmaceutical composition, the liquid vehicle or a combination thereof further comprises a preservative, an antioxidant, a buffering agent, an acidifying agent, saline, an electrolyte, another therapeutic agent, an alkalizing agent, an antimicrobial agent, an antifungal agent, solubility enhancing agent, emulsifying agent, complexation enhancing agent, antifoaming agent, oil, or a combination thereof.

52. The pharmaceutical kit of claim 51 wherein the other therapeutic agent is present and is a local anesthetic agent.

53. The pharmaceutical kit of claim 52, wherein the local anesthetic agent is selected from the group consisting of, procaine, lidocaine, piperocaine, tetracaine, lignocaine, prilocaine, bupivacaine, proxymetacaine, ropivacaine, dibucaine and a combination thereof.

54. The formulation of claim 1, 3, 2, 4, 5–6 or 7, wherein the formulation possesses a greater photochemical stability to fluorescent and/or ultraviolet light than does an emulsion type formulation comprising water, egg lecithin, oil, glycerol, preservative and a comparable amount of propofol.

55. The formulation of claim 8, wherein the formulation possesses a greater photochemical stability to fluorescent and/or ultraviolet light than does an emulsion type formulation comprising water, egg lecithin, oil, glycerol, preservative and a comparable amount of propofol.

56. The formulation of claim 9, wherein the formulation possesses a greater photochemical stability to fluorescent and/or ultraviolet light than does an emulsion type formulation comprising water, egg lecithin, oil, glycerol, preservative and a comparable amount of propofol.

57. The formulation of claim 11, wherein the formulation possesses a greater photochemical stability to fluorescent and/or ultraviolet light than does an emulsion type formulation comprising water, egg lecithin, oil, glycerol, preservative and a comparable amount of propofol.

58. The formulation of claim 13, 14, 15 or 16, wherein the formulation possesses a greater photochemical stability to fluorescent and/or ultraviolet light than does an emulsion type formulation comprising water, egg lecithin, oil, glycerol, preservative and a comparable amount of propofol.

59. The formulation of claim 17, wherein the formulation possesses a greater photochemical stability to fluorescent and/or ultraviolet light than does an emulsion type formulation comprising water, egg lecithin, oil, glycerol, preservative and a comparable amount of propofol.

60. The formulation of claim 18, wherein the formulation possesses a greater photochemical stability to fluorescent and/or ultraviolet light than does an emulsion type formulation comprising water, egg lecithin, oil, glycerol, preservative and a comparable amount of propofol.

61. The formulation of claim 19, wherein the formulation possesses a greater photochemical stability to fluorescent and/or ultraviolet light than does an emulsion type formulation comprising water, egg lecithin, oil, glycerol, preservative and a comparable amount of propofol.

\* \* \* \* \*